(12) United States Patent
Martens et al.

(10) Patent No.: US 7,223,896 B2
(45) Date of Patent: May 29, 2007

(54) FINES CO-FEED FOR MAINTAINING EFFICIENT REACTOR HYDRODYNAMICS

(75) Inventors: Luc R. M. Martens, Meise (BE); James R. Lattner, Seabrook, TX (US); Rutton D. Patel, Arlington, VA (US); David C. Skouby, Centreville, VA (US); Stephen Neil Vaughn, Kingwood, TX (US); Yun-feng Chang, Houston, TX (US); Jesse F. Goellner, Houston, TX (US); Mareel J. Janssen, Kessel-Lo (BE); Richard C. Senior, Fairfax, VA (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 380 days.

(21) Appl. No.: 10/835,494

(22) Filed: Apr. 29, 2004

(65) Prior Publication Data

US 2005/0245781 A1 Nov. 3, 2005

(51) Int. Cl.
*C07C 1/00* (2006.01)
*B07B 7/00* (2006.01)
*C10G 45/00* (2006.01)

(52) U.S. Cl. .................. 585/634; 209/154; 208/152
(58) Field of Classification Search ........ 585/638–640; 208/152; 209/154
See application file for complete search history.

(56) References Cited

U.S. PATENT DOCUMENTS

| 2,573,559 | A | 10/1951 | Friedman ................. 260/449.6 |
| 3,527,694 | A | 9/1970 | Luckenbach ............... 208/118 |
| 4,935,568 | A | 6/1990 | Harandi et al. ............ 585/300 |
| 5,079,379 | A | 1/1992 | Braun et al. .............. 558/324 |
| 5,521,133 | A | 5/1996 | Koermer et al. .............. 502/9 |
| 5,746,321 | A | 5/1998 | Hettinger, Jr. et al. ...... 209/233 |
| 6,010,619 | A | 1/2000 | Wise et al. ........... 208/120.01 |
| 6,541,415 | B2 | 4/2003 | Vaughn et al. .............. 502/214 |
| 6,710,008 | B2* | 3/2004 | Chang et al. ............... 502/214 |
| 2003/0125598 | A1 | 7/2003 | Chisholm et al. ........... 585/640 |

(Continued)

FOREIGN PATENT DOCUMENTS

CA 940854 1/1974

(Continued)

OTHER PUBLICATIONS

Grace, J.R. et al, "Fines Concentration in Voids in Fluidized Beds", Powder Technology, vol. 62, No. 2, Aug. 1990, pp. 203-205.

(Continued)

*Primary Examiner*—Glenn Caldarda
*Assistant Examiner*—In Suk Bullock
(74) *Attorney, Agent, or Firm*—David M. Weisberg

(57) ABSTRACT

This invention provides processes for maintaining a desired particle size distribution in an oxygenate to olefin reaction system. In one embodiment, the invention comprises replacing lost catalyst fines with less active co-catalyst particles. By adding less active co-catalyst particles to the reaction system, desirable fluidization characteristics and hydrodynamics can be maintained without affecting the overall (or primary catalyst) performance and product selectivities. The invention is also directed to a population of catalyst particles having a desirable particle size distribution well-suited for realizing ideal fluidization and hydrodynamic characteristics.

68 Claims, 1 Drawing Sheet

U.S. PATENT DOCUMENTS

2003/0135079 A1  7/2003  Chang et al. ............... 585/640

FOREIGN PATENT DOCUMENTS

| EP | 0 040 914 | 2/1981 |
| --- | --- | --- |
| EP | 0 148 024 | 10/1985 |
| GB | 1305973 | 2/1973 |
| JP | 74027263 | 7/1974 |
| WO | WO 97/39300 | 10/1997 |
| WO | WO 2004/014793 | 2/2004 |
| WO | WO 2004/029009 | 8/2004 |

OTHER PUBLICATIONS

G. Yaluris, Ph.D., et al., "The Effects of Fe Poisoning on FCC Catalysts," 2001 NPRA Annual Meeting, pp. 1-26.

S. Purnell et al., "A Comprehensive Approach to Catalyst Design for Resid Applications," 2003 NPRA Annual Meeting, pp. 1-22.

M. Raterman, "FCC Catalyst Flow-Problem Predictions," Oil & Gas Journal, Jan. 7, 1985.

D. Geldart, et al., "The Effect of Fines on Entrainment From Gas Fluidised Beds," Trans IChemE, vol. 57, pp. 269-275 (1979).

Thomson Derwent 2002 Abstract of JP 74027263, published Jul. 16, 1974.

U.S. Appl. No. 10/634,557 filed Aug. 6, 2003 (Inventor—Marcel Janssen) entitled "Molecular Sieve Catalyst Compositions, Their Production And Use In Conversion Processes." (2003B078).

Abrahamsen, A.R. and Geldart, D., Behaviour of Gas Fluidized Beds of Fine Powders, Powder Technol., 26, pp. 35-46 (1980).

Geldart, D., and Radthke, A.L., The Effect of Particle Properties on the Behavior of Equilibrium Cracking Catalysts on Standpipe Flow, Powder Technol., pp. 47-55, 57-65 and 157-165 (1986).

Steenge, W.D.E., Dane, F., and Parker, W.A., Fluidization Behavior of FCC Catalyst: Effects of Catalyst Properties and Gas Distribution, presented at the Katalistiks' 8th Annual Fluid Catalytic Cracking Symposium, Budapest, Hungary, Jun. (1987).

\* cited by examiner

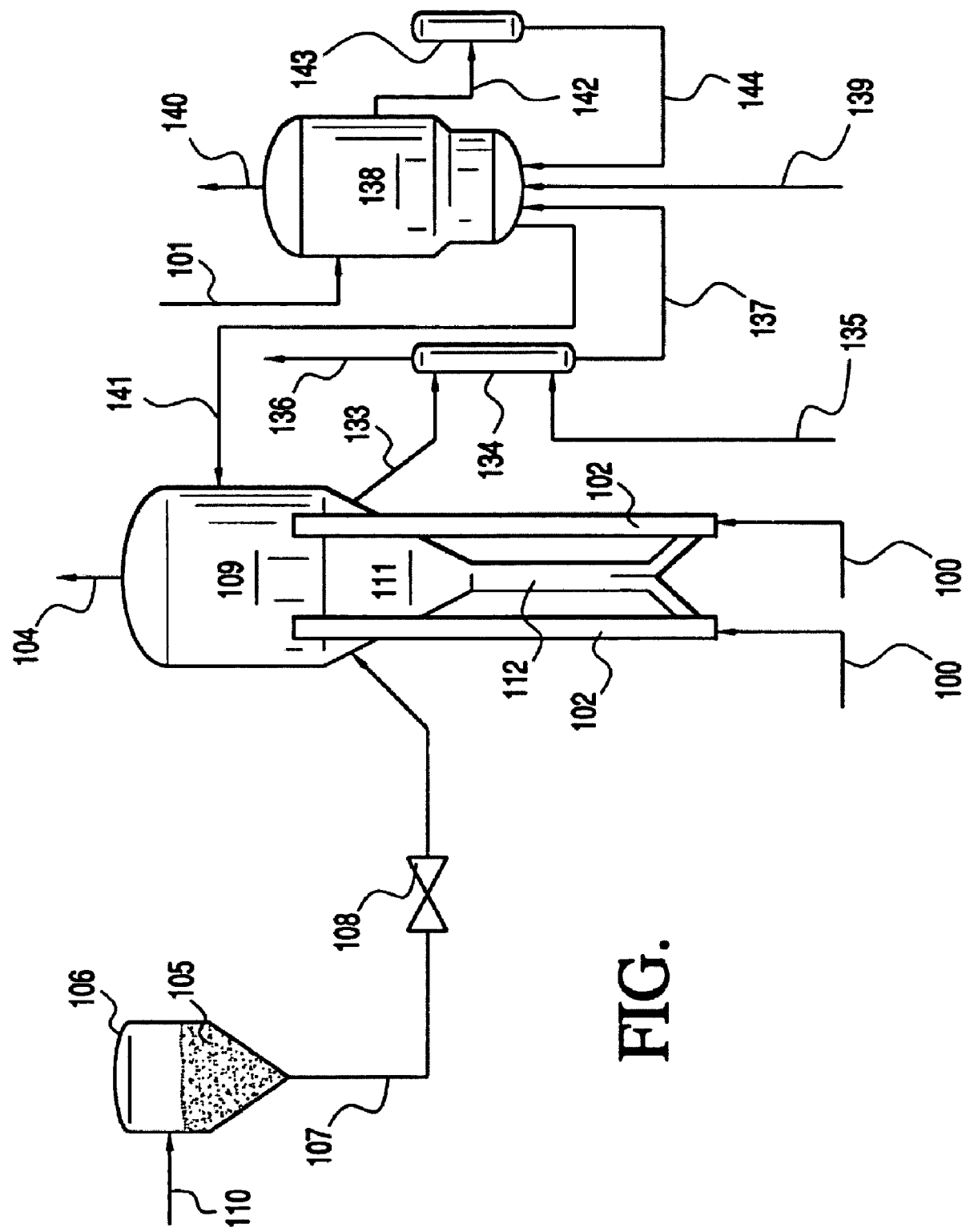
FIG.

FINES CO-FEED FOR MAINTAINING EFFICIENT REACTOR HYDRODYNAMICS

FIELD OF THE INVENTION

The present invention relates to processes and systems for maintaining desirable particle size characteristics in reaction systems. Specifically, the invention relates to selectively adding co-catalyst particles to reaction systems, preferably oxygenate to olefin reaction systems, in order to maintain desirable particle size distributions therein.

BACKGROUND OF THE INVENTION

Light olefins, defined herein as ethylene and propylene, serve as feeds for the production of numerous chemicals. Olefins traditionally are produced by petroleum cracking. Because of the limited supply and/or the high cost of petroleum sources, the cost of producing olefins from petroleum sources has increased steadily.

Oxygenates such as alcohols, particularly methanol, dimethyl ether, and ethanol, are alternative feedstocks for the production of light olefins. Alcohols may be produced by fermentation, or from synthesis gas derived from natural gas, petroleum liquids, carbonaceous materials, including coal, recycled plastics, municipal wastes, or any organic material. Because of the wide variety of sources, alcohol, alcohol derivatives, and other oxygenates have promise as an economical, non-petroleum source for olefin production.

In an oxygenate to olefin (OTO) reaction system, an oxygenate in an oxygenate-containing feedstock contacts a molecular sieve catalyst composition under conditions effective to convert at least a portion of the oxygenate to light olefins, which are yielded from the reaction system in a reaction effluent. As the feedstock contacts the molecular sieve catalyst compositions at high weight hourly space velocities and under elevated temperature and pressure conditions, a portion of the catalyst compositions can break up, e.g., attrite, to form one or more smaller attrited catalyst particles. Some catalyst attrition particles are very small in size and are referred to as catalyst fines. Due to their relatively high surface area to mass ratios, a portion of the catalyst fines in the reaction system may become undesirably entrained with the reaction effluent and exit the reaction system therewith. Conversely, due to their relatively low surface area to mass ratios, larger particles tend to be selectively retained in OTO reaction systems. The selective retention of larger particles is particularly a problem for highly attrition resistant particles.

The build up of large catalyst particles in an OTO reaction system produces two undesirable effects. First, in a large particle rich reaction system, the circulating fluid bed will not operate as well, particularly with regard to circulation of catalyst within the standpipes and also with regard to gas distribution within a fluidized bed. Second, the large particles that are selectively retained in the reaction system will tend to lose their effectiveness, e.g., activity and selectivity, with time. That is, the build up of large particles in the reaction system is undesirable because the larger particles will tend to decrease the overall effectiveness of the collection of catalyst particles contained in the reaction system.

One conventional technique for removing undesirably-sized catalyst particles includes non-selectively removing a fraction of all of the catalyst particles in the reaction system to make room for the addition of fresh catalyst. This technique for removing undesirably-sized catalyst particles is inefficient, however, because a significant portion of the desirably-sized catalyst particles are removed from the reaction system with the undesirably-sized catalyst particles.

U.S. Pat. No. 5,746,321 to Hettinger, Jr. et al. discloses the combination of a magnetic separator, a catalyst classifier, and/or a catalyst attriter, which wears off the outer layers of catalyst, yields more active catalyst of lower metal content with closer control of average particles size, and narrows particle size distribution providing improved fluidization properties and better activity and selectivity. The process is especially useful when processing high metal-containing feedstocks.

U.S. Pat. No. 2,573,559 to Friedman discloses replacing a bed of fluidized catalyst, which has become reduced in activity during use, with fresh fluidized catalyst, the average particle size of both catalysts being in the range of 40-400 mesh. The average size of the fresh catalyst differs from that of the partially spent catalyst by at least 10-mesh size and preferably 25 mesh. The fresh catalyst is introduced into the reactor under conditions such that the reaction temperature is not substantially increased, and at the same time catalyst is withdrawn from the reactor at a portion below the top level of the bed. The catalyst withdrawn is separated by particle size into fresh catalyst, which is returned to the reactor, and deactivated catalyst, which is regenerated. According to the '559 patent, the complete replacement of catalyst can be accomplished under normal operating conditions in from 20 to 48 hours.

In view of the importance of maintaining desirably-sized catalyst particles in reaction systems, particularly in OTO reaction systems, improved processes are sought for maintaining a desired particle size distribution in an OTO reaction system.

SUMMARY OF THE PRESENT INVENTION

The present invention provides processes and systems for maintaining a desired particle size distribution in an oxygenate to olefin (OTO) reaction system. The loss of catalyst fines from such reaction systems may result in undesirable fluidization and hydrodynamic characteristics. In one embodiment, the invention comprises replacing lost catalyst fines with less reactive co-catalyst particles. By adding less reactive co-catalyst particles to the reaction system, desirable fluidization characteristics and hydrodynamics can be maintained without affecting the overall (or primary catalyst) performance and product selectivities. The invention is also directed to a population of catalyst particles having a desirable particle size distribution well-suited for realizing ideal fluidization and hydrodynamic characteristics.

In one embodiment, the invention is directed to a process for maintaining a desired particle size distribution in a reaction system, preferably an OTO reaction system. In this embodiment, the reaction system preferably comprises a reaction zone and a disengaging zone. The process includes a step of feeding a plurality of catalyst particles into the reaction zone. The plurality of catalyst particles comprise catalyst fines and catalyst non-fines, and has a first $k_{max}$ value for light olefins. The invention also comprises a step of contacting the plurality of catalyst particles with a feedstock in the reaction zone under conditions effective to convert at least a portion of the feedstock to product. The product and the plurality of catalyst particles are directed from the reaction zone to the disengaging zone. An effluent stream, comprising at least a majority of the product and at least a portion of the catalyst fines, is yielded from the disengaging zone. Co-catalyst particles, having a second $k_{max}$ value less than the first $k_{max}$ value, are added to the reaction system. At least a majority of the catalyst non-fines are directed from the disengaging zone to the reaction zone.

In another embodiment, the invention is directed to a process for maintaining a specifically defined particle size distribution in a reaction system. In this process, the invention includes a step of feeding a plurality of catalyst particles into a reaction zone. The plurality of catalyst particles has a $d_2$ of at least about 7 microns, a $d_{10}$ of less than about 45 microns, a $d_{50}$ between about 75 and about 100 microns, and a $d_{90}$ of less than about 150 microns. The plurality of catalyst particles contacts a feedstock in the reaction zone under conditions effective to convert at least a portion of the feedstock to product. The product and the plurality of catalyst particles are directed to a disengaging zone. The product and a portion of catalyst fines are yielded from the disengaging zone under conditions effective to increase one or more of the $d_2$, the $d_{10}$, the $d_{50}$ and the $d_{90}$ to provide an increased $d_2$, an increased $d_{10}$, an increased $d_{50}$ or an increased $d_{90}$. One or more of the increased $d_2$, the increased $d_{10}$, the increased $d_{50}$ or the increased $d_{90}$ are then decreased by adding co-catalyst particles to the reaction system.

In another embodiment, the invention is directed to a process for maintaining a particle size distribution in a reaction system. This process includes a step of providing a plurality of catalyst particles in a reaction zone, wherein the plurality of catalyst particles has a $d_2$ of at least about 7 microns, a first median particle diameter (preferably between about 75 microns and about 90 microns), and a $d_{90}$ of less than about 150 microns (preferably no greater than about 120 microns). The plurality of catalyst particles comprises primary catalyst particles. The primary catalyst particles contact a feedstock, preferably an oxygenate such as methanol, in the reaction zone under conditions effective to convert at least a portion of the feedstock to product, e.g., light olefins. The product and the plurality of catalyst particles are directed to a disengaging zone. The first median particle diameter is increased to a second median particle diameter by losing a portion of catalyst fines from the disengaging zone. The second median particle diameter is decreased to a third median particle diameter by adding co-catalyst particles to the reaction system.

In another embodiment, the invention is directed to a plurality of catalyst particles having a specific particle size distribution. In this embodiment the particle size distribution comprises: (a) a $d_2$ of at least about 7 microns (preferably at least about 20 microns); (b) a $d_{10}$ of less than about 45 microns; (c) a $d_{50}$ between about 75 and about 100 microns; and (d) a $d_{90}$ of no greater than about 150 microns.

In another embodiment, the invention is directed to a process for maintaining desirable fluidization characteristics in a reactor. In this embodiment, the process includes the step of providing a first plurality of catalyst particles in a reactor, wherein the first plurality of catalyst particles comprises catalyst fines and catalyst non-fines and has a first fluidization index. A product and a portion of the catalyst fines are yielded from the reactor to form a second plurality of catalyst particles in the reactor, wherein the second plurality of catalyst particles has a second fluidization index less than the first fluidization index. Co-catalyst particles are added to the reaction system to form a third plurality of catalyst particles in the reactor, wherein the third plurality of catalyst particles has a third fluidization index greater than the second fluidization index.

BRIEF DESCRIPTION OF THE DRAWING

The present invention will be better understood in view of the attached non-limiting FIGURE, which illustrates a schematic flow diagram of one embodiment of the present invention.

DETAILED DESCRIPTION OF THE INVENTION

Introduction

This invention provides processes for maintaining a desired particle size distribution in an oxygenate to olefin (OTO) reaction system. The loss of catalyst fines from such reaction systems may result in undesirable fluidization and hydrodynamic characteristics. In one embodiment, the invention comprises replacing lost catalyst fines with less reactive co-catalyst particles. Additionally or alternatively, the reaction system comprises a catalyst regenerator, and the co-catalyst particles enhance regeneration in the catalyst regenerator. By adding less reactive co-catalyst particles to the reaction system, desirable fluidization characteristics and hydrodynamics can be maintained without affecting the overall (or primary catalyst) performance and product selectivities. The invention is also directed to a population of catalyst particles having a desirable particle size distribution well-suited for realizing ideal fluidization and hydrodynamic characteristics.

Molecular Sieves and Catalysts Thereof

The present invention, in one embodiment, is directed to adding co-catalyst particles (also referred to as secondary catalyst particles) to a reaction system, which comprises primary catalyst particles. Preferably, the primary catalyst particles are molecular sieve catalyst compositions comprising molecular sieves. Depending on the desired activity of the co-catalyst particles for converting oxygenates to light olefins, the co-catalyst particles may or may not comprise molecular sieves.

Molecular sieves have various chemical, physical, and framework characteristics. Molecular sieves have been well classified by the Structure Commission of the International Zeolite Association according to the rules of the IUPAC Commission on Zeolite Nomenclature. A molecular sieve's "framework-type" describes the connectivity and topology of the tetrahedrally coordinated atoms constituting the framework, and makes an abstraction of the specific properties for those materials. Framework-type zeolite and zeolite-type molecular sieves for which a structure has been established are assigned a three letter code and are described in the Atlas of Zeolite Framework Types, 5th edition, Elsevier, London, England (2001), which is herein fully incorporated by reference.

Non-limiting examples of these molecular sieves are the small pore molecular sieves, AEI, AFT, APC, ATN, ATT, ATV, AWW, BIK, CAS, CHA, CHI, DAC, DDR, EDI, ERI, GOO, KFI, LEV, LOV, LTA, MON, PAU, PHI, RHO, ROG, THO, and substituted forms thereof; the medium pore molecular sieves, AFO, AEL, EUO, HEU, FER, MEL, MFI, MTW, MTT, TON, and substituted forms thereof; and the large pore molecular sieves, EMT, FAU, and substituted forms thereof. Other molecular sieves include ANA, BEA, CFI, CLO, DON, GIS, LTL, MER, MOR, MWW and SOD. Non-limiting examples of the preferred molecular sieves, particularly for converting an oxygenate containing feedstock into olefin(s), include AEL, AFY, BEA, CHA, EDI, FAU, FER, GIS, LTA, LTL, MER, MFI, MOR, MTT, MWW, TAM and TON. In one preferred embodiment, the molecular sieve of the invention has an AEI framework-type or a CHA framework-type, or a combination thereof, most preferably a CHA framework-type.

Molecular sieve materials all have 3-dimensional framework structure of corner-sharing $TO_4$ tetrahedral, where T is any tetrahedrally coordinated cation. These molecular sieves are typically described in terms of the size of the ring that defines a pore, where the size is based on the number of T atoms in the ring. Other framework-type characteristics include the arrangement of rings that form a cage, and when present, the dimension of channels, and the spaces between the cages. See van Bekkum, et al., Introduction to Zeolite Science and Practice, Second Completely Revised and Expanded Edition, Volume 137, pages 1-67, Elsevier Science, B. V., Amsterdam, Netherlands (2001).

The small, medium and large pore molecular sieves have from a 4-ring to a 12-ring or greater framework-type. In a preferred embodiment, the zeolitic molecular sieves have 8-, 10- or 12-ring structures or larger and an average pore size in the range of from about 3 Å to 15 Å. In the most preferred embodiment, the molecular sieves of the invention, preferably silicoaluminophosphate molecular sieves, have 8-rings and an average pore size less than about 5 Å, preferably in the range of from about 3 Å to about 5 Å, more preferably from 3 Å to about 4.5 Å, and most preferably from 3.5 Å to about 4.2 Å.

Molecular sieves, particularly zeolitic and zeolitic-type molecular sieves, preferably have a molecular framework of one, preferably two or more corner-sharing $[TO_4]$ tetrahedral units, more preferably, two or more $[SiO_4]$, $[AlO_4]$ and/or $[PO_4]$ tetrahedral units, and most preferably $[SiO_4]$, $[AlO_4]$ and $[PO_4]$ tetrahedral units. These silicon, aluminum, and phosphorous based molecular sieves and metal containing silicon, aluminum and phosphorous based molecular sieves have been described in detail in numerous publications including for example, U.S. Pat. No. 4,567,029 (MeAPO where Me is Mg, Mn, Zn, or Co), U.S. Pat. No. 4,440,871 (SAPO), European Patent Application EP-A-0 159 624 (ELAPSO where El is As, Be, B, Cr, Co, Ga, Ge, Fe, Li, Mg, Mn, Ti or Zn), U.S. Pat. No. 4,554,143 (FeAPO), U.S. Pat. Nos. 4,822,478, 4,683,217, 4,744,885 (FeAPSO), EP-A-0 158 975 and U.S. Pat. No. 4,935,216 (ZnAPSO, EP-A-0 161 489 (CoAPSO), EP-A-0 158 976 (ELAPO, where EL is Co, Fe, Mg, Mn, Ti or Zn), U.S. Pat. No. 4,310,440 (AlPO4), EP-A-0 158 350 (SENAPSO), U.S. Pat. No. 4,973,460 (LiAPSO), U.S. Pat. No. 4,789,535 (LiAPO), U.S. Pat. No. 4,992,250 (GeAPSO), U.S. Pat. No. 4,888,167 (GeAPO), U.S. Pat. No. 5,057,295 (BAPSO), U.S. Pat. No. 4,738,837 (CrAPSO), U.S. Pat. Nos. 4,759,919, and 4,851,106 (CrAPO), U.S. Pat. Nos. 4,758,419, 4,882,038, 5,434,326 and 5,478,787 (MgAPSO), U.S. Pat. No. 4,554,143 (FeAPO), U.S. Pat. No. 4,894,213 (AsAPSO), U.S. Pat. No. 4,913,888 (AsAPO), U.S. Pat. Nos. 4,686,092, 4,846,956 and 4,793,833 (MnAPSO), U.S. Pat. Nos. 5,345,011 and 6,156,931 (MnAPO), U.S. Pat. No. 4,737,353 (BeAPSO), U.S. Pat. No. 4,940,570 (BeAPO), U.S. Pat. Nos. 4,801,309, 4,684,617 and 4,880,520 (TiAPSO), U.S. Pat. Nos. 4,500,651, 4,551,236 and 4,605,492 (TiAPO), U.S. Pat. Nos. 4,824,554, 4,744,970 (CoAPSO), U.S. Pat. No. 4,735,806 (GaAPSO) EP-A-0 293 937 (QAPSO, where Q is framework oxide unit $[QO_2]$), as well as U.S. Pat. Nos. 4,567,029, 4,686,093, 4,781,814, 4,793,984, 4,801,364, 4,853,197, 4,917,876, 4,952,384, 4,956,164, 4,956,165, 4,973,785, 5,241,093, 5,493,066 and 5,675,050, all of which are fully incorporated herein by reference. Other molecular sieves are described in R. Szostak, Handbook of Molecular Sieves, Van Nostrand Reinhold, New York, N.Y. (1992), which is fully incorporated herein by reference.

The more preferred silicon, aluminum and/or phosphorous containing molecular sieves, and aluminum, phosphorous, and optionally silicon containing molecular sieves include aluminophosphate (ALPO) molecular sieves and silicoaluminophosphate (SAPO) molecular sieves and substituted, preferably metal substituted, ALPO and SAPO molecular sieves. The most preferred molecular sieves are SAPO molecular sieves, and metal substituted SAPO molecular sieves. In an embodiment, the metal is an alkali metal of Group IA of the Periodic Table of Elements, an alkaline earth metal of Group IIA of the Periodic Table of Elements, a rare earth metal of Group IIIB, including the Lanthanides: lanthanum, cerium, praseodymium, neodymium, samarium, europium, gadolinium, terbium, dysprosium, holmium, erbium, thulium, ytterbium and lutetium; and scandium or yttrium of the Periodic Table of Elements, a transition metal of Groups IVB, VB, VIB, VIIB, VIIIB, and IB of the Periodic Table of Elements, or mixtures of any of these metal species. In one preferred embodiment, the metal is selected from the group consisting of Co, Cr, Cu, Fe, Ga, Ge, Mg, Mn, Ni, Sn, Ti, Zn and Zr, and mixtures thereof. In another preferred embodiment, these metal atoms discussed above are inserted into the framework of a molecular sieve through a tetrahedral unit, such as $[MeO_2]$, and carry a net charge depending on the valence state of the metal substituent. For example, in one embodiment, when the metal substituent has a valence state of +2, +3, +4, +5, or +6, the net charge of the tetrahedral unit is between −2 and +2.

In one embodiment, the molecular sieve, as described in many of the U.S. patents mentioned above, is represented by the empirical formula, on an anhydrous basis:

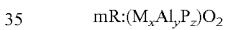

$$mR:(M_xAl_yP_z)O_2$$

wherein R represents at least one templating agent, preferably an organic templating agent; m is the number of moles of R per mole of $(M_xAl_yP_z)O_2$ and m has a value from 0 to 3, preferably from 0 to 2, and most preferably from 0 to 1; x, y, and z represent the mole fraction of M, Al and P as tetrahedral oxides, where M is a metal selected from one of Group IA, IIA, IB, IIIB, IVB, VB, VIB, VIIB, VIIIB and Lanthanide's of the Periodic Table of Elements, preferably M is selected from one of the group consisting of Co, Cr, Cu, Fe, Ga, Ge, Mg, Mn, Ni, Sn, Ti, Zn and Zr. In an embodiment, m is greater than or equal to 0.2, and x, y and z are greater than or equal to 0.01. In another embodiment, m is greater than 0.1 to about 1, x is greater than 0 to about 0.25, y is in the range of from 0.4 to 0.5, and z is in the range of from 0.25 to 0.5, more preferably m is from 0.15 to 0.7, x is from 0.01 to 0.2, y is from 0.4 to 0.5, and z is from 0.3 to 0.5.

Non-limiting examples of SAPO and ALPO molecular sieves of the invention include one or a combination of SAPO-5, SAPO-8, SAPO-11, SAPO-16, SAPO-17, SAPO-18, SAPO-20, SAPO-31, SAPO-34, SAPO-35, SAPO-36, SAPO-37, SAPO-40, SAPO-41, SAPO-42, SAPO-44 (U.S. Pat. No. 6,162,415), SAPO-47, SAPO-56, ALPO-5, ALPO-11, ALPO-18, ALPO-31, ALPO-34, ALPO-36, ALPO-37, ALPO-46, and metal containing molecular sieves thereof. Preferably, the molecular sieve is selected from the group consisting of SAPO-5, SAPO-8, SAPO-11, SAPO-16, SAPO-17, SAPO-18, SAPO-20, SAPO-31, SAPO-34, SAPO-35, SAPO-36, SAPO-37, SAPO-40, SAPO-41, SAPO-42, SAPO-44, SAPO-47, SAPO-56, the metal containing forms thereof, and mixtures thereof. The more preferred zeolite-type molecular sieves include one or a combination of SAPO-18, SAPO-34, SAPO-35, SAPO-44, SAPO-56, ALPO-18 and ALPO-34, even more preferably one or a combination of SAPO-1 8, SAPO-34, ALPO-34 and ALPO-18, and metal containing molecular sieves thereof, and most preferably one or a combination of SAPO-34 and ALPO-18, and metal containing molecular sieves thereof. Optionally, the molecular sieve is selected from the group consisting of SAPO-34, the metal containing forms thereof, and mixtures thereof.

In an embodiment, the molecular sieve is an intergrowth material having two or more distinct phases of crystalline structures within one molecular sieve composition. In particular, intergrowth molecular sieves are described in the U.S. patent application Ser. No. 09/924,016 filed Aug. 7, 2001 and PCT WO 98/15496 published Apr. 16, 1998, both of which are herein fully incorporated by reference. For example, SAPO-18, ALPO-18 and RUW-18 have an AEI framework-type, and SAPO-34 has a CHA framework-type. In another embodiment, the molecular sieve comprises at least one intergrown phase of AEI and CHA framework-types, preferably the molecular sieve has a greater amount of CHA framework-type to AEI framework-type, and more preferably the molar ratio of CHA to AEI is greater than 1:1.

Molecular Sieve Synthesis

The synthesis of molecular sieves is described in many of the references discussed above. Generally, molecular sieves are synthesized by the hydrothermal crystallization of one or more of a source of aluminum, a source of phosphorous, a source of silicon, a templating agent, and a metal containing compound. Typically, a combination of sources of silicon, aluminum and phosphorous, optionally with one or more templating agents and/or one or more metal containing compounds are placed in a sealed pressure vessel, optionally lined with an inert plastic such as polytetrafluoroethylene, and heated, under a crystallization pressure and temperature, until a crystalline molecular sieve material is formed, and then recovered by filtration, centrifugation and/or decanting.

In a preferred embodiment, the molecular sieves are synthesized by forming a reaction product of a source of silicon, a source of aluminum, a source of phosphorous, and/or an organic templating agent, preferably a nitrogen containing organic templating agent. This particularly preferred embodiment results in the synthesis of a silicoaluminophosphate crystalline material that is then isolated by filtration, centrifugation and/or decanting.

Non-limiting examples of silicon sources include silicates, fumed silica, for example, Aerosil-200 available from Degussa Inc., New York, N.Y., and CAB-O-SIL M-5, silicon compounds such as tetraalkyl orthosilicates, for example, tetramethyl orthosilicate (TMOS) and tetraethylorthosilicate (TEOS), colloidal silicas or aqueous suspensions thereof, for example Ludox-HS-40 sol available from E.I. du Pont de Nemours, Wilmington, Del., silicic acid, alkali-metal silicate, or any combination thereof. The preferred source of silicon is a silica sol.

Non-limiting examples of aluminum sources include aluminum-containing compositions such as aluminum alkoxides, for example aluminum isopropoxide, aluminum phosphate, aluminum hydroxide, sodium aluminate, pseudo-boehmite, gibbsite and aluminum trichloride, or any combinations thereof. A preferred source of aluminum is pseudo-boehmite, particularly when producing a silicoaluminophosphate molecular sieve.

Non-limiting examples of phosphorous sources, which may also include aluminum-containing phosphorous compositions, include phosphorous-containing, inorganic or organic, compositions such as phosphoric acid, organic phosphates such as triethyl phosphate, and crystalline or amorphous aluminophosphates such as ALPO4, phosphorous salts, or combinations thereof. The preferred source of phosphorous is phosphoric acid, particularly when producing a silicoaluminophosphate.

Templating agents are generally compounds that contain elements of Group VA of the Periodic Table of Elements, particularly nitrogen, phosphorus, arsenic and antimony, more preferably nitrogen or phosphorous, and most preferably nitrogen. Typical templating agents of Group VA of the Periodic Table of elements also contain at least one alkyl or aryl group, preferably an alkyl or aryl group having from 1 to 10 carbon atoms, and more preferably from 1 to 8 carbon atoms. The preferred templating agents are nitrogen-containing compounds such as amines and quaternary ammonium compounds.

The quaternary ammonium compounds, in one embodiment, are represented by the general formula $R_4N+$, where each R is hydrogen or a hydrocarbyl or substituted hydrocarbyl group, preferably an alkyl group or an aryl group having from 1 to 10 carbon atoms. In one embodiment, the templating agents include a combination of one or more quaternary ammonium compound(s) and one or more of a mono-, di- or tri-amine.

Non-limiting examples of templating agents include tetraalkyl ammonium compounds including salts thereof such as tetramethyl ammonium compounds including salts thereof, tetraethyl ammonium compounds including salts thereof, tetrapropyl ammonium including salts thereof, and tetrabutylammonium including salts thereof, cyclohexylamine, morpholine, di-n-propylamine (DPA), tripropylamine, triethylamine (TEA), triethanolamine, piperidine, cyclohexylamine and substituted cyclohexylamines, 2-methylpyridine, N,N-dimethylbenzylamine, N,N-diethylethanolamine, dicyclohexylamine, N,N-dimethylethanolamine, choline, N,N'-dimethylpiperazine, 1,4-diazabicyclo(2,2,2) octane, N',N',N,N-tetramethyl-(1,6)hexanediamine, N-methyldiethanolamine, N-methyl-ethanolamine, N-methyl piperidine, 3-methyl-piperidine, N-methylcyclohexylamine, 3-methylpyridine, 4-methyl-pyridine, quinuclidine, N,N'-dimethyl-1,4-diazabicyclo(2,2,2)octane ion; di-n-butylamine, neopentylamine, di-n-pentylamine, isopropylamine, t-butyl-amine, ethylenediamine, pyrrolidine, polyethylenimine and 2-imidazolidone.

The preferred templating agent or template is a tetraethylammonium compound, such as tetraethyl ammonium hydroxide (TEAOH), tetraethyl ammonium phosphate, tetraethyl ammonium fluoride, tetraethyl ammonium bromide, tetraethyl ammonium chloride and tetraethyl ammonium acetate. The most preferred templating agent is tetraethyl ammonium hydroxide and salts thereof, particularly when producing a silicoaluminophosphate molecular sieve. In one embodiment, a combination of two or more of any of the above templating agents is used in combination with one or more of a silicon-, aluminum-, and phosphorous-source.

A synthesis mixture containing at a minimum a silicon-, aluminum-, and/or phosphorous-composition, and a templating agent, should have a pH in the range of from 2 to 10, preferably in the range of from 4 to 9, and most preferably in the range of from 5 to 8. Generally, the synthesis mixture is sealed in a vessel and heated, preferably under autogenous pressure, to a temperature in the range of from about 80° C. to about 250° C., and more preferably from about 150° C. to about 180° C. The time required to form the crystalline product is typically from immediately up to several weeks, the duration of which is usually dependent on the temperature; the higher the temperature the shorter the duration. Typically, the crystalline molecular sieve product is formed, usually in a slurry state, and is recovered by any standard technique well known in the art, for example centrifugation or filtration. The isolated or separated crystalline product, in an embodiment, is washed, typically, using a liquid such as water, from one to many times. The washed crystalline product is then optionally dried, preferably in air.

Molecular sieves have either a high silicon (Si) to aluminum (Al) atomic ratio or a low silicon to aluminum atomic ratio, however, a low Si/Al ratio is preferred for SAPO synthesis. In one embodiment, the molecular sieve has a Si/Al ratio less than 0.65, preferably less than 0.40, more preferably less than 0.32, and most preferably less than 0.20. In another embodiment the molecular sieve has a Si/Al ratio in the range of from about 0.65 to about 0.10, preferably from about 0.40 to about 0.10, more preferably from about 0.32 to about 0.10, and more preferably from about 0.32 to about 0.15.

Once the molecular sieve is synthesized as described above, depending on the requirements of the particular conversion process, the molecular sieve is then formulated into a molecular sieve catalyst composition as described in more detail below. The molecular sieves synthesized above are made or formulated into molecular sieve catalyst compositions by combining the synthesized molecular sieve(s) optionally with one or more matrix materials and optionally a binder to form a formulation composition.

Matrix materials are typically effective in reducing overall catalyst cost, act as thermal sinks assisting in shielding heat from the catalyst composition for example during regeneration, densifying the catalyst composition, increasing catalyst strength such as crush strength and attrition resistance, and to control the rate of conversion in a particular process.

Non-limiting examples of matrix materials include one or more of: rare earth metals, non-active, metal oxides including titania, zirconia, magnesia, thoria, beryllia, quartz, silica or sols, and mixtures thereof, for example silica-magnesia, silica-zirconia, silica-titania, silica-alumina and silica-alumina-thoria. In an embodiment, matrix materials are natural clays such as those from the families of montmorillonite and kaolin. These natural clays include kaolins known as, for example, Dixie, McNamee, Georgia and Florida clays. Non-limiting examples of other matrix materials include: haloysite, kaolinite, dickite, nacrite, or anauxite. In one embodiment, the matrix material, preferably any of the clays, are subjected to well known modification processes such as calcination and/or acid treatment and/or chemical treatment.

In one preferred embodiment, the matrix material is selected for its high content of a Group VIII metal, such as iron, in order to enhance the coke combusting characteristics of the catalyst composition (or co-catalyst composition), as described in detail below. Alternatively, the clay or clay-type composition has a low iron, cobalt, nickel, titanium, palladium, chromium and/or platinum content. In one embodiment, the matrix material is a clay or a clay-type composition and most preferably the matrix material is kaolin. Kaolin has been found to form a pumpable, high solid content slurry, it has a low fresh surface area, and it packs together easily due to its platelet structure. A preferred average particle size of the matrix material, most preferably kaolin, is from about 0.1 µm to about 0.6 µm with a $d_{90}$ particle size distribution of less than about 1 µm.

Forming Molecular Sieve Catalyst Compositions

As indicated above, once the molecular sieve is synthesized, depending on the requirements of the particular conversion process, the molecular sieve is then formulated into a molecular sieve catalyst composition as described in more detail below. The molecular sieves synthesized above are made or formulated into molecular sieve catalyst compositions by combining the synthesized molecular sieve(s) with a matrix a binder and optionally a matrix material to form a formulation composition. This formulation composition is formed into useful shape and sized particles by well-known techniques such as spray drying, pelletizing, extrusion, and the like, spray drying being the most preferred. It is also preferred that after spray drying for example that the formulation composition is then calcined.

In one embodiment, the weight ratio of the binder to the molecular sieve is in the range of from about 0.1 to 0.5, preferably in the range of from 0.1 to less than 0.5, more preferably in the range of from 0.11 to 0.48, even more preferably from 0.12 to about 0.45, yet even more preferably from 0.13 to less than 0.45, and most preferably in the range of from 0.15 to about 0.4. In another embodiment, the weight ratio of the binder to the molecular sieve is in the range of from 0.11 to 0.45, preferably in the range of from about 0.12 to less than 0.40, more preferably in the range of from 0.15 to about 0.35, and most preferably in the range of from 0.2 to about 0.3. All values between these ranges are included in this patent specification.

In another embodiment, the molecular sieve catalyst composition or formulated molecular sieve catalyst composition has a micropore surface area (MSA) measured in $m^2$/g-molecular sieve that is about 70 percent, preferably about 75 percent, more preferably 80 percent, even more preferably 85 percent, and most preferably about 90 percent of the MSA of the molecular sieve itself. The MSA of the molecular sieve catalyst composition is the total MSA of the composition divided by the fraction of the molecular sieve contained in the molecular sieve catalyst composition.

There are many different binders that are useful in forming the molecular sieve catalyst composition. Non-limiting examples of binders that are useful alone or in combination include various types of hydrated alumina, silicas, and/or other inorganic oxide sol. One preferred alumina containing sol is aluminum chlorhydrate. The inorganic oxide sol acts like glue binding the synthesized molecular sieves and other materials such as the matrix together, particularly after thermal treatment. Upon heating, the inorganic oxide sol, preferably having a low viscosity, is converted into an inorganic oxide matrix component. For example, an alumina sol will convert to an aluminum oxide matrix following heat treatment.

Aluminum chlorhydrate, a hydroxylated aluminum based sol containing a chloride counter ion, has the general formula of $Al_mO_n(OH)_oCl_p\cdot x(H_2O)$ wherein m is 1 to 20, n is 1 to 8, o is 5 to 40, p is 2 to 15, and x is 0 to 30. In one embodiment, the binder is $Al_{13}O_4(OH)_{24}Cl_7\cdot 12(H_2O)$ as is described in G. M. Wolterman, et al., Stud. Surf. Sci. and Catal., 76, pages 105-144 (1993), which is herein incorporated by reference. In another embodiment, one or more binders are combined with one or more other non-limiting examples of alumina materials such as aluminum oxyhydroxide, γ-alumina, boehmite, diaspore, and transitional aluminas such as α-alumina, β-alumina, γ-alumina, δ-alumina, ε-alumina, κ-alumina, and ρ-alumina, aluminum trihydroxide, such as gibbsite, bayerite, nordstrandite, doyelite, and mixtures thereof.

In another embodiment, the binders are alumina sols, predominantly comprising aluminum oxide, optionally including some silicon. In yet another embodiment, the binders are peptized alumina made by treating alumina hydrates such as pseudobohemite, with an acid, preferably an acid that does not contain a halogen, to prepare sols or aluminum ion solutions. Non-limiting examples of commercially available colloidal alumina sols include Nalco 8676 available from Nalco Chemical Co., Naperville, Ill., and Nyacol AL20DW, available from Nyacol Nano Technologies, Inc., Ashland, Mass.

In one embodiment, the binder, the synthesized molecular sieve and the matrix material are combined in the presence of a liquid slurrying medium such as water to form a molecular sieve catalyst composition, where the amount of binder is from about 2% by weight to about 30% by weight, preferably from about 5% by weight to about 20% by weight, and more preferably from about 7% by weight to about 15% by weight, based on the total weight of the binder, the molecular sieve and matrix material, excluding the liquid.

Upon combining the synthesized molecular sieve and the binder, optionally with a matrix material, in a liquid to form a slurry, mixing, preferably rigorous mixing is needed to produce a substantially homogeneous mixture containing the synthesized molecular sieve. Non-limiting examples of suitable liquid slurrying mediums include one or a combination of water, alcohol, ketones, aldehydes, and/or esters. The most preferred liquid is water. In one embodiment, the slurry is colloid-milled for a period of time sufficient to produce the desired slurry texture, sub-particle size, and/or sub-particle size distribution.

The liquid containing synthesized molecular sieve and matrix material, and the optional binder, are in the same or different liquid, and are combined in any order, together, simultaneously, sequentially, or a combination thereof. In the preferred embodiment, the same liquid, preferably water is used.

The molecular sieve catalyst composition in a preferred embodiment is made by preparing a slurry containing a molecular sieve, a matrix material and a binder. The solids content of the preferred slurry includes from about 20% to about 80% by weight molecular sieve, preferably from about 30% to about 65% by weight molecular sieve, more preferably from about 35% to about 55% by weight molecular sieve, from about 5% to about 30%, preferably from about 5% to about 25%, by weight of binder, and about 20% to about 80%, preferably about 30% to about 60%, by weight matrix material.

In another most preferred embodiment, the solids content in a slurry comprising a molecular sieve, a binder, and optionally a matrix material, and a liquid medium is in the range of from about 20 weight percent to about 80 weight percent, more preferably in the range of from 30 weight percent to about 70 weight percent, even more preferably in the range of from 35 weight percent to 60 weight percent, still even more preferably from about 36 weight percent to about 50 weight percent, yet even more preferably in the range of from 37 weight percent to about 49 weight percent, and most preferably in the range of from 38 weight percent to about 48 weight percent.

As the slurry is mixed, the solids in the slurry aggregate preferably to a point where the slurry contains solid molecular sieve catalyst composition particles. It is preferable that these particles are small and have a uniform size distribution such that the $d_{90}$ diameter of these particles is less than 20 μm, more preferably less than 15 μm, and most preferably less than 10 μm. In one embodiment, the slurry of the invention comprises at least 90 percent by volume of the molecular sieve catalyst composition particles comprising the molecular sieve, binder, and optionally matrix material, have a diameter of less than 20 μm, preferably less than 15 μm, and most preferably less than 10 μm.

In one preferred embodiment the slurry comprises a liquid portion and solid portion, wherein the solid portion comprises solid particles, the solid particles comprising a molecular sieve, a binder and a matrix material; wherein the slurry comprises in the range of from about 30 weight percent to about 55 weight percent solid particles, preferably from about 35 weight percent to 50 weight percent, and at least 90 percent of the solid particles having a diameter less than 20 μm, preferably less than 10 μm.

In one embodiment, the slurry of the synthesized molecular sieve, binder and matrix material is mixed or milled to achieve a sufficiently uniform slurry of sub-particles of the molecular sieve catalyst composition to form a formulation composition that is then fed to a forming unit that produces the molecular sieve catalyst composition or formulated molecular sieve catalyst composition. In a preferred embodiment, the forming unit is a spray dryer. Typically, the forming unit is maintained at a temperature sufficient to remove most of the liquid from the slurry, and from the resulting molecular sieve catalyst composition. The resulting catalyst composition when formed in this way takes the form of microspheres.

When a spray drier is used as the forming unit, typically, any one or a combination of the slurries described above, more particularly a slurry of the synthesized molecular sieve, matrix material, and binder, is co-fed to the spray dryer with a drying gas with an average inlet temperature ranging from 200° C. to 550° C., and a combined outlet temperature ranging from 100° C. to about 225° C. In an embodiment, the average diameter of the spray dried formed catalyst composition is from about 40 μm to about 300 μm, preferably from about 50 μm to about 250 μm, more preferably from about 55 μm to about 200 μm, and most preferably from about 65 μm to about 90 μm.

During spray drying, the slurry is passed through a nozzle distributing the slurry into small droplets, resembling an aerosol spray, and into a drying chamber. Atomization is achieved by forcing the slurry through a single nozzle or multiple nozzles with a pressure drop in the range of from 100 psig to 7,000 psig (690 kpag to 48265 kpag), preferably from 100 psig to 4,000 psig (690 kpag to 27580 kpag). In another embodiment, the slurry is co-fed through a single nozzle or multiple nozzles along with an atomization fluid such as air, steam, flue gas, or any other suitable gas with a pressure drop preferably in the range of from 1 psig to 150 psig (6.9 kpag to 1034 kpag).

In yet another embodiment, the slurry described above is directed to the perimeter of a spinning wheel that distributes the slurry into small droplets, the size of which is controlled by many factors including slurry viscosity, surface tension, flow rate, pressure, and temperature of the slurry, the shape and dimension of the nozzle(s), or the spinning rate of the wheel. These droplets are then dried in a co-current or counter-current flow of air passing through a spray drier to form a substantially dried or dried molecular sieve catalyst composition, more specifically a molecular sieve composition in a powder or a microsphere form.

Generally, the size of the microspheres is controlled to some extent by the solids content of the slurry. However, control of the size of the catalyst composition and its spherical characteristics are controllable by varying the slurry feed properties and conditions of atomization. In one embodiment, the catalyst composition has a $d_{50}$ particle size from about 20 to about 200 microns.

Other processes for forming a molecular sieve catalyst composition are described in U.S. patent application Ser. No. 09/617,714 filed Jul. 17, 2000 (spray drying using a recycled molecular sieve catalyst composition), which is herein incorporated by reference.

In another embodiment, the formulated molecular sieve catalyst composition comprises from about 1% to about 99%, preferably from about 10% to about 90%, more preferably from about 10% to about 80%, even more preferably from about 20% to about 70%, and most preferably from about 25% to about 60% by weight of the molecular sieve based on the total weight of the molecular sieve catalyst composition.

Once the molecular sieve catalyst composition is formed in a substantially dry or dried state, to further harden and/or activate the formed catalyst composition, a heat treatment such as calcination, at an elevated temperature is preferably performed. A conventional calcination environment is air that typically includes a small amount of water vapor. Typical calcination temperatures are in the range from about 400° C. to about 1,000° C., preferably from about 500° C. to about 800° C., and most preferably from about 550° C. to about 700° C., preferably in a calcination environment such as air, nitrogen, helium, flue gas (combustion product lean in oxygen), or any combination thereof. In one embodiment, calcination of the formulated molecular sieve catalyst composition is carried out in any number of well known devices including rotary calciners, fluid bed calciners, batch ovens, and the like. Calcination time is typically dependent on the degree of hardening of the molecular sieve catalyst composition and the temperature ranges from about 15 minutes to about 20 hours. In a preferred embodiment, the molecular sieve catalyst composition is heated in nitrogen at a temperature of from about 600° C. to about 700° C. Heating is carried out for a period of time typically from 15 minutes to 15 hours, preferably from 30 minutes to about 10 hours, more preferably from about 30 minutes to about 5 hours.

In one preferred embodiment of the invention, the molecular sieve catalyst composition or formulated molecular sieve catalyst composition comprises a synthesized molecular sieve in an amount of from 20 weight percent to 60 weight percent, a binder in an amount of from 5 to 30 weight percent, and a matrix material in an amount of from 0 to 70 weight percent based on the total weight of the catalyst composition, upon calcination, and the catalyst composition having weight ratio of binder to sieve of from 0.1 to less than 0.5. In addition, the catalyst composition of this embodiment has an MSA on a contained sieve basis of the molecular sieve by itself from 450 m²/g-molecular sieve to 550 m²/g-molecular sieve, and/or an ARI less than 2 weight percent per hour.

As discussed above, the co-catalyst particles utilized in the present invention may or may not comprise molecular sieves. Optionally, the co-catalyst particles comprise molecular sieves, but they comprise a smaller weight fraction of molecular sieves than the primary catalyst particles. In another embodiment, the co-catalyst particles comprise a different type of molecular sieve than contained in the primary catalyst particles. In this latter embodiment, the molecular sieves contained in the co-catalyst particles optionally are less active for converting oxygenates to light olefins than the molecular sieves contained in the primary catalyst particles.

These various types of co-catalyst particles containing molecular sieves may be formed in a manner similar to the processes for manufacturing the primary catalyst particles, described in detail above. For formation of the co-catalyst particles, however, a smaller amount of molecular sieve particles and/or a different less reactive type of molecular sieve may be added to the slurry during co-catalyst manufacture.

Co-catalyst particles not comprising molecular sieves may also be formed as described above, but without adding molecular sieves to the slurry. For example, the co-catalyst particles optionally are comprised of a matrix material, with or without binder. Optionally, the co-catalyst particles are selected from the group consisting of silica, alumina, aluminosilicates, clay, and mixtures thereof. Optionally, the co-catalyst particles consist essentially of a component selected from the group consisting of: silica, alumina, aluminosilicates, clay and mixtures thereof. Optionally, the co-catalyst particles comprise a component selected from the group consisting of: silica, alumina, aluminosilicates, clay and mixtures thereof. In one embodiment, the co-catalyst particles comprise a basic oxide or hydrotalcite, a rare earth metal component, and optionally a molecular sieve.

Reaction Systems Implementing Molecular Sieve Catalyst Compositions

The molecular sieve catalyst compositions or formulated molecular sieve catalyst compositions described above are useful in a variety of processes including: cracking, of for example a naphtha feed to light olefin(s) (U.S. Pat. No. 6,300,537) or higher molecular weight (MW) hydrocarbons to lower MW hydrocarbons; hydrocracking, of for example heavy petroleum and/or cyclic feedstock; isomerization, of for example aromatics such as xylene, polymerization, of for example one or more olefin(s) to produce a polymer product; reforming; hydrogenation; dehydrogenation; dewaxing, of for example hydrocarbons to remove straight chain paraffins; absorption, of for example alkyl aromatic compounds for separating out isomers thereof; alkylation, of for example aromatic hydrocarbons such as benzene and alkyl benzene, optionally with propylene to produce cumene or with long chain olefins; transalkylation, of for example a combination of aromatic and polyalkylaromatic hydrocarbons; dealkylation; hydrodecylization; disproportionation, of for example toluene to make benzene and paraxylene; oligomerization, of for example straight and branched chain olefin(s); and dehydrocyclization.

Preferred processes are conversion processes including: naphtha to highly aromatic mixtures; light olefin(s) to gasoline, distillates and lubricants; oxygenates to olefin(s); light paraffins to olefins and/or aromatics; and unsaturated hydrocarbons (ethylene and/or acetylene) to aldehydes for conversion into alcohols, acids and esters. The most preferred process of the invention is a process directed to the conversion of a feedstock comprising one or more oxygenates to one or more olefin(s).

The molecular sieve catalyst compositions described above are particularly useful in conversion processes of different feedstock. Typically, the feedstock contains one or more aliphatic-containing compounds that include alcohols, amines, carbonyl compounds for example aldehydes, ketones and carboxylic acids, ethers, halides, mercaptans, sulfides, and the like, and mixtures thereof. The aliphatic moiety of the aliphatic-containing compounds typically contains from 1 to about 50 carbon atoms, preferably from 1 to 20 carbon atoms, more preferably from 1 to 10 carbon atoms, and most preferably from 1 to 4 carbon atoms.

Non-limiting examples of aliphatic-containing compounds include: alcohols such as methanol and ethanol, alkyl-mercaptans such as methyl mercaptan and ethyl mercaptan, alkyl-sulfides such as methyl sulfide, alkyl-amines such as methyl amine, alkyl-ethers such as dimethyl ether, diethyl ether and methylethyl ether, alkyl-halides such as methyl chloride and ethyl chloride, alkyl ketones such as dimethyl ketone, formaldehydes, and various acids such as acetic acid.

In a preferred embodiment of the process of the invention, the feedstock comprises one or more oxygenates, more specifically, one or more organic compound(s) containing at least one oxygen atom. In the most preferred embodiment of the process of invention, the oxygenate in the feedstock is one or more alcohol(s), preferably aliphatic alcohol(s) where the aliphatic moiety of the alcohol(s) has from 1 to 20 carbon atoms, preferably from 1 to 10 carbon atoms, and most preferably from 1 to 4 carbon atoms. The alcohols useful as feedstock in the process of the invention include lower straight and branched chain aliphatic alcohols and their unsaturated counterparts.

Non-limiting examples of oxygenates include methanol, ethanol, n-propanol, isopropanol, methyl ethyl ether, dimethyl ether, diethyl ether, di-isopropyl ether, formaldehyde, dimethyl carbonate, dimethyl ketone, acetic acid, and mixtures thereof. In the most preferred embodiment, the feedstock is selected from one or more of methanol, ethanol, dimethyl ether, diethyl ether or a combination thereof, more preferably methanol and dimethyl ether, and most preferably methanol.

The various feedstocks discussed above, particularly a feedstock comprising an oxygenate, more particularly a feedstock comprising an alcohol, is converted primarily into one or more olefin(s). The olefin(s) or olefin monomer(s) produced from the feedstock typically have from 2 to 30 carbon atoms, preferably 2 to 8 carbon atoms, more preferably 2 to 6 carbon atoms, still more preferably 2 to 4 carbons atoms, and most preferably ethylene an/or propylene. Non-limiting examples of olefin monomer(s) include ethylene, propylene, butene-1, pentene-1, 4-methyl-pentene-1, hexene-1, octene-1 and decene-1, preferably ethylene, propylene, butene-1, pentene-1, 4-methyl-pentene-1, hexene-1, octene-1 and isomers thereof. Other olefin monomer(s) include unsaturated monomers, diolefins having 4 to 18 carbon atoms, conjugated or nonconjugated dienes, polyenes, vinyl monomers and cyclic olefins.

In the most preferred embodiment, the feedstock, preferably of one or more oxygenates, is converted in the presence of a molecular sieve catalyst composition of the invention into olefin(s) having 2 to 6 carbons atoms, preferably 2 to 4 carbon atoms. Most preferably, the olefin(s), alone or combination, are converted from a feedstock containing an oxygenate, preferably an alcohol, most preferably methanol, to the preferred olefin(s) ethylene and/or propylene.

There are many processes used to convert feedstock into olefin(s) including various cracking processes such as steam cracking, thermal regenerative cracking, fluidized bed cracking, fluid catalytic cracking, deep catalytic cracking, and visbreaking. The most preferred process is generally referred to as gas-to-olefins (GTO) or alternatively, methanol-to-olefins (MTO). In a GTO process, typically natural gas is converted into a synthesis gas that is converted into an oxygenated feedstock, preferably containing methanol, where the oxygenated feedstock is converted in the presence of a molecular sieve catalyst composition into one or more olefin(s), preferably ethylene and/or propylene. In a MTO process, typically an oxygenated feedstock, most preferably a methanol containing feedstock, is converted in the presence of a molecular sieve catalyst composition thereof into one or more olefin(s), preferably and predominantly, ethylene and/or propylene, often referred to as light olefin(s).

In one embodiment of the process for converting a feedstock, preferably a feedstock comprising one or more oxygenates, the amount of olefin(s) produced based on the total weight of hydrocarbon produced is greater than 50 weight percent, preferably greater than 60 weight percent, more preferably greater than 70 weight percent, and most preferably greater than 75 weight percent. In another embodiment of the process for conversion of one or more oxygenates to one or more olefin(s), the amount of ethylene and/or propylene produced based on the total weight of hydrocarbon product produced is greater than 65 weight percent, preferably greater than 70 weight percent, more preferably greater than 75 weight percent, and most preferably greater than 78 weight percent.

In another embodiment of the process for conversion of one or more oxygenates to one or more olefin(s), the amount of ethylene produced in weight percent based on the total weight of hydrocarbon product produced, is greater than 30 weight percent, more preferably greater than 35 weight percent, and most preferably greater than 40 weight percent. In yet another embodiment of the process for conversion of one or more oxygenates to one or more olefin(s), the amount of propylene produced in weight percent based on the total weight of hydrocarbon product produced is greater than 20 weight percent, preferably greater than 25 weight percent, more preferably greater than 30 weight percent, and most preferably greater than 35 weight percent.

The feedstock, in one embodiment, contains one or more diluent(s), typically used to reduce the concentration of the feedstock, and are generally non-reactive to the feedstock or molecular sieve catalyst composition. Non-limiting examples of diluents include helium, argon, nitrogen, carbon monoxide, carbon dioxide, water, essentially non-reactive paraffins (especially alkanes such as methane, ethane, and propane), essentially non-reactive aromatic compounds, and mixtures thereof. The most preferred diluents are water and nitrogen, with water being particularly preferred.

The diluent, water for example, is used either in a liquid or a vapor form, or a combination thereof. The diluent is either added directly to a feedstock entering into a reactor or added directly into a reactor, or added with a molecular sieve catalyst composition. In one embodiment, the amount of diluent in the feedstock is in the range of from about 1 to about 99 mole percent based on the total number of moles of the feedstock and diluent, preferably from about 1 to 80 mole percent, more preferably from about 5 to about 50, and most preferably from about 5 to about 25.

In one embodiment, other hydrocarbons are added to a feedstock either directly or indirectly, and include olefin(s), paraffin(s), aromatic(s) (see for example U.S. Pat. No. 4,677,242, addition of aromatics) or mixtures thereof, preferably propylene, butylene, pentylene, and other hydrocarbons having 4 or more carbon atoms, or mixtures thereof.

The process for converting a feedstock, especially a feedstock containing one or more oxygenates, in the presence of a molecular sieve catalyst composition of the invention, is carried out in a reaction process in a reactor, where the process is a fixed bed process, a fluidized bed process (includes a turbulent bed process), preferably a continuous fluidized bed process, and most preferably a continuous high velocity fluidized bed process.

The reaction processes can take place in a variety of catalytic reactors such as hybrid reactors that have a dense bed or fixed bed reaction zones and/or fast fluidized bed reaction zones coupled together, circulating fluidized bed reactors, riser reactors, and the like. Suitable conventional reactor types are described in for example U.S. Pat. No. 4,076,796, U.S. Pat. No. 6,287,522 (dual riser), and Fluidization Engineering, D. Kunii and O. Levenspiel, Robert E. Krieger Publishing Company, New York, N.Y. 1977, which are all herein fully incorporated by reference. The preferred reactor type are riser reactors generally described in Riser Reactor, Fluidization and Fluid-Particle Systems, pages 48 to 59, F. A. Zenz and D. F. Othmer, Reinhold Publishing Corporation, New York, 1960, and U.S. Pat. No. 6,166,282 (fast-fluidized bed reactor), and U.S. patent application Ser. No. 09/564,613 filed May 4, 2000 (multiple riser reactor), which are all herein fully incorporated by reference.

In the preferred embodiment, a fluidized bed process or high velocity fluidized bed process includes a reactor system, a regeneration system and a recovery system.

The reactor system preferably is a fluid bed reactor system having a first reaction zone within one or more riser reactor(s) and a second reaction zone within at least one disengaging vessel, preferably comprising one or more cyclones. In one embodiment, the one or more riser reactor(s) and disengaging vessel is contained within a single reactor vessel. Fresh feedstock, preferably containing one or more oxygenates, optionally with one or more diluent(s), is fed to the one or more riser reactor(s) in which a molecular sieve catalyst composition or coked version thereof is introduced. In one embodiment, the molecular sieve catalyst composition or coked version thereof is contacted with a liquid or gas, or combination thereof, prior to being introduced to the riser reactor(s), preferably the liquid is water or methanol, and the gas is an inert gas such as nitrogen.

In an embodiment, the amount of liquid feedstock fed separately or jointly with a vapor feedstock, to a reactor system is in the range of from 0.1 weight percent to about 85 weight percent, preferably from about 1 weight percent to about 75 weight percent, more preferably from about 5 weight percent to about 65 weight percent based on the total weight of the feedstock including any diluent contained therein. The liquid and vapor feedstocks are preferably of similar or the same composition, or contain varying proportions of the same or different feedstock with the same or different diluent.

The feedstock entering the reactor system is preferably converted, partially or fully, in the first reaction zone into a gaseous effluent that enters the disengaging vessel along with a coked molecular sieve catalyst composition. In the preferred embodiment, cyclone(s) within the disengaging vessel are designed to separate the molecular sieve catalyst composition, preferably a coked molecular sieve catalyst composition, from the gaseous effluent containing one or more olefin(s) within the disengaging zone. Cyclones are preferred, however, gravity effects within the disengaging vessel will also separate the catalyst compositions from the gaseous effluent. Other methods for separating the catalyst compositions from the gaseous effluent include the use of plates, caps, elbows, and the like.

In one embodiment of the disengaging system, the disengaging system includes a disengaging vessel, typically a lower portion of the disengaging vessel is a stripping zone. In the stripping zone the coked molecular sieve catalyst composition is contacted with a gas, preferably one or a combination of steam, methane, carbon dioxide, carbon monoxide, hydrogen, or an inert gas such as argon, preferably steam, to recover adsorbed hydrocarbons from the coked molecular sieve catalyst composition that is then introduced to the regeneration system. In another embodiment, the stripping zone is in a separate vessel from the disengaging vessel and the gas is passed at a gas hourly superficial velocity (GHSV) of from 1 hr$^{-1}$ to about 20,000 hr$^{-1}$ based on the volume of gas to volume of coked molecular sieve catalyst composition, preferably at an elevated temperature from 250° C. to about 750° C., preferably from about 350° C. to 650° C., over the coked molecular sieve catalyst composition.

The conversion temperature employed in the conversion process, specifically within the reactor system, is in the range of from about 200° C. to about 1000° C., preferably from about 250° C. to about 800° C., more preferably from about 250° C. to about 750 ° C., yet more preferably from about 300° C. to about 650° C., yet even more preferably from about 350° C. to about 600° C. most preferably from about 350° C. to about 550° C.

The conversion pressure employed in the conversion process, specifically within the reactor system, varies over a wide range including autogenous pressure. The conversion pressure is based on the partial pressure of the feedstock exclusive of any diluent therein. Typically the conversion pressure employed in the process is in the range of from about 0.1 kPaa to about 5 MPaa, preferably from about 5 kPaa to about 1 MPaa, and most preferably from about 20 kPaa to about 500 kPaa.

The weight hourly space velocity (WHSV), particularly in a process for converting a feedstock containing one or more oxygenates in the presence of a molecular sieve catalyst composition within a reaction zone, is defined as the total weight of the feedstock excluding any diluents to the reaction zone per hour per weight of molecular sieve in the molecular sieve catalyst composition in the reaction zone. The WHSV is maintained at a level sufficient to keep the catalyst composition in a fluidized state within a reactor.

Typically, the WHSV ranges from about 1 hr$^{-1}$ to about 5000 hr$^{-1}$, preferably from about 2 hr$^{-1}$ to about 3000 hr$^{-1}$, more preferably from about 5 hr$^{-1}$ to about 1500 hr$^{-1}$, and most preferably from about 10 hr$^{-1}$ to about 1000 hr$^{-1}$. In one preferred embodiment, the WHSV is greater than 20 hr$^{-1}$, preferably the WHSV for conversion of a feedstock containing methanol and dimethyl ether is in the range of from about 20 hr$^{-1}$ to about 300 hr$^{-1}$.

The superficial gas velocity (SGV) of the feedstock including diluent and reaction products within the reactor system is preferably sufficient to fluidize the molecular sieve catalyst composition within a reaction zone in the reactor. The SGV in the process, particularly within the reactor system, more particularly within the riser reactor(s), is at least 0.1 meter per second (m/sec), preferably greater than 0.5 m/sec, more preferably greater than 1 m/sec, even more preferably greater than 2 m/sec, yet even more preferably greater than 3 m/sec, and most preferably greater than 4 m/sec. See for example U.S. patent application Ser. No. 09/708,753 filed Nov. 8, 2000, which is herein incorporated by reference.

In one preferred embodiment of the process for converting an oxygenate to olefin(s) using a silicoaluminophosphate molecular sieve catalyst composition, the process is operated at a WHSV of at least 20 hr$^{-1}$ and a Temperature Corrected Normalized Methane Selectivity (TCNMS) of less than 0.016, preferably less than or equal to 0.01. See for example U.S. Pat. No. 5,952,538, which is herein fully incorporated by reference. In another embodiment of the processes for converting an oxygenate such as methanol to one or more olefin(s) using a molecular sieve catalyst composition, the WHSV is from 0.01 hr$^{-1}$ to about 100 hr$^{-1}$, at a temperature of from about 350° C. to 550° C., and silica to $Me_2O_3$ (Me is a Group IIIA or VIII element from the Periodic Table of Elements) molar ratio of from 300 to 2500. See for example EP-0 642 485 B1, which is herein fully incorporated by reference. Other processes for converting an oxygenate such as methanol to one or more olefin(s) using a molecular sieve catalyst composition are described in PCT WO 01/23500 published Apr. 5, 2001 (propane reduction at an average catalyst feedstock exposure of at least 1.0), which is herein incorporated by reference.

The coked molecular sieve catalyst composition is withdrawn from the disengaging vessel, preferably by one or more cyclones(s), and introduced to the regeneration system. The regeneration system comprises a regenerator where the coked catalyst composition is contacted with a regeneration medium, preferably a gas containing oxygen, under general regeneration conditions of temperature, pressure and residence time. Non-limiting examples of the regeneration medium include one or more of oxygen, $O_3$, $SO_3$, $N_2O$, NO, $NO_2$, $N_2O_5$, air, air diluted with nitrogen or carbon dioxide, oxygen and water (U.S. Pat. No. 6,245,703), carbon monoxide and/or hydrogen. The regeneration conditions are those capable of burning coke from the coked catalyst composition, preferably to a level less than 0.5 weight percent based on the total weight of the coked molecular sieve catalyst composition entering the regeneration system. The coked molecular sieve catalyst composition withdrawn from the regenerator forms a regenerated molecular sieve catalyst composition.

The regeneration temperature is in the range of from about 200° C. to about 1500° C., preferably from about 300° C. to about 1000° C., more preferably from about 450° C. to about 750° C., and most preferably from about 550° C. to 700° C. The regeneration pressure is in the range of from about 15 psia (103 kPaa) to about 500 psia (3448 kPaa), preferably from about 20 psia (138 kPaa) to about 250 psia (1724 kPaa), more preferably from about 25 psia (172 kPaa) to about 150 psia (1034 kPaa), and most preferably from about 30 psia (207 kPaa) to about 60 psia (414 kPaa). The preferred residence time of the molecular sieve catalyst composition in the regenerator is in the range of from about one minute to several hours, most preferably about one minute to 100 minutes, and the preferred volume of oxygen in the gas is in the range of from about 0.01 mole percent to about 5 mole percent based on the total volume of the gas.

In one embodiment, regeneration promoters, typically metal containing compounds such as platinum, palladium and the like, are added to the regenerator directly, or indirectly, for example with the coked catalyst composition. Also, in another embodiment, a fresh molecular sieve catalyst composition is added to the regenerator containing a regeneration medium of oxygen and water as described in U.S. Pat. No. 6,245,703, which is herein fully incorporated by reference. In yet another embodiment, a portion of the coked molecular sieve catalyst composition from the regenerator is returned directly to the one or more riser reactor(s), or indirectly, by pre-contacting with the feedstock, or contacting with fresh molecular sieve catalyst composition, or contacting with a regenerated molecular sieve catalyst composition or a cooled regenerated molecular sieve catalyst composition described below.

The burning of coke is an exothermic reaction, and in an embodiment, the temperature within the regeneration system is controlled by various techniques in the art including feeding a cooled gas to the regenerator vessel, operated either in a batch, continuous, or semi-continuous mode, or a combination thereof. A preferred technique involves withdrawing the regenerated molecular sieve catalyst composition from the regeneration system and passing the regenerated molecular sieve catalyst composition through a catalyst cooler that forms a cooled regenerated molecular sieve catalyst composition. The catalyst cooler, in an embodiment, is a heat exchanger that is located either internal or external to the regeneration system. In one embodiment, the cooler regenerated molecular sieve catalyst composition is returned to the regenerator in a continuous cycle, alternatively, (see U.S. patent application Ser. No. 09/587,766 filed Jun. 6, 2000) a portion of the cooled regenerated molecular sieve catalyst composition is returned to the regenerator vessel in a continuous cycle, and another portion of the cooled molecular sieve regenerated molecular sieve catalyst composition is returned to the riser reactor(s), directly or indirectly, or a portion of the regenerated molecular sieve catalyst composition or cooled regenerated molecular sieve catalyst composition is contacted with by-products within the gaseous effluent (PCT WO 00/49106 published Aug. 24, 2000), which are all herein fully incorporated by reference. In another embodiment, a regenerated molecular sieve catalyst composition contacted with an alcohol, preferably ethanol, 1-propanol, 1-butanol or mixture thereof, is introduced to the reactor system, as described in U.S. patent application Ser. No. 09/785,122 filed Feb. 16, 2001, which is herein fully incorporated by reference. Other methods for operating a regeneration system are in disclosed U.S. Pat. No. 6,290,916 (controlling moisture), which is herein fully incorporated by reference.

The regenerated molecular sieve catalyst composition withdrawn from the regeneration system, preferably from the catalyst cooler, is combined with a fresh molecular sieve catalyst composition and/or re-circulated molecular sieve catalyst composition and/or feedstock and/or fresh gas or liquids, and returned to the riser reactor(s). In another embodiment, the regenerated molecular sieve catalyst composition withdrawn from the regeneration system is returned to the riser reactor(s) directly, optionally after passing through a catalyst cooler. In one embodiment, a carrier, such as an inert gas, feedstock vapor, steam or the like, semi-continuously or continuously, facilitates the introduction of the regenerated molecular sieve catalyst composition to the reactor system, preferably to the one or more riser reactor(s).

In one embodiment, by controlling the flow of the regenerated molecular sieve catalyst composition or cooled regenerated molecular sieve catalyst composition from the regeneration system to the reactor system, the optimum level of coke on the molecular sieve catalyst composition in the reaction zone is maintained. There are many techniques for controlling the flow of a molecular sieve catalyst composition described in Michel Louge, Experimental Techniques, Circulating Fluidized Beds, Grace, Avidan and Knowlton, eds., Blackie, 1997 (336-337), which is herein incorporated by reference. In another embodiment, the optimum level of coke on the molecular sieve catalyst composition in the reaction zone is maintained by controlling the flow rate of oxygen containing gas flowing to the regenerator, a partial regeneration. Coke levels on the molecular sieve catalyst composition is measured by withdrawing from the conversion process the molecular sieve catalyst composition at a point in the process and determining its carbon content. Typical levels of coke on the molecular sieve catalyst composition, after regeneration is in the range of from 0.01 weight percent to about 15 weight percent, preferably from about 0.1 weight percent to about 10 weight percent, more preferably from about 0.2 weight percent to about 5 weight percent, and most preferably from about 0.3 weight percent to about 2 weight percent based on the total weight of the molecular sieve and not the total weight of the molecular sieve catalyst composition.

In one preferred embodiment, the mixture of fresh molecular sieve catalyst composition and/or regenerated molecular sieve catalyst composition and/or cooled regenerated molecular sieve catalyst composition in the reaction zone contains in the range of from about 1 to 50 weight percent, preferably from about 2 to 30 weight percent, more preferably from about 2 to about 20 weight percent, and most preferably from about 2 to about 10 coke or carbonaceous deposit based on the total weight of the mixture of molecular sieve catalyst compositions. See for example U.S. Pat. No. 6,023,005, which is herein fully incorporated by reference. It is recognized that the molecular sieve catalyst composition in the reaction zone is made up of a mixture of regenerated and fresh molecular sieve catalyst composition that have varying levels of carbon and carbon-like deposits, e.g., coke. The measured level of these deposits, specifically coke, represents an average of the levels on individual molecular sieve catalyst composition particles.

The gaseous effluent is withdrawn from the disengaging system and is passed through a recovery system. There are many well known recovery systems, techniques and sequences that are useful in separating olefin(s) and purifying olefin(s) from the gaseous effluent. Recovery systems generally comprise one or more or a combination of a various separation, fractionation and/or distillation towers, columns, splitters, or trains, reaction systems such as ethylbenzene manufacture (U.S. Pat. No. 5,476,978) and other derivative processes such as aldehydes, ketones and ester manufacture (U.S. Pat. No. 5,675,041), and other associated equipment for example various condensers, heat exchangers, refrigeration systems or chill trains, compressors, knock-out drums or pots, pumps, and the like. Non-limiting examples of these towers, columns, splitters or trains used alone or in combination include one or more of a demethanizer, preferably a high temperature demethanizer, a dethanizer, a depropanizer, preferably a wet depropanizer, a wash tower often referred to as a caustic wash tower and/or quench tower, absorbers, adsorbers, membranes, ethylene (C2) splitter, propylene (C3) splitter, butene (C4) splitter, and the like.

Various recovery systems useful for recovering predominately olefin(s), preferably prime or light olefin(s) such as ethylene, propylene and/or butene are described in U.S. Pat. No. 5,960,643 (secondary rich ethylene stream), U.S. Pat. Nos. 5,019,143, 5,452,581 and 5,082,481 (membrane separations), U.S. Pat. No. 5,672,197 (pressure dependent adsorbents), U.S. Pat. No. 6,069,288 (hydrogen removal), U.S. Pat. No. 5,904,880 (recovered methanol to hydrogen and carbon dioxide in one step), U.S. Pat. No. 5,927,063 (recovered methanol to gas turbine power plant), and U.S. Pat. No. 6,121,504 (direct product quench), U.S. Pat. No. 6,121,503 (high purity olefins without superfractionation), and U.S. Pat. No. 6,293,998 (pressure swing adsorption), which are all herein fully incorporated by reference.

Generally accompanying most recovery systems is the production, generation or accumulation of additional products, by-products and/or contaminants along with the preferred prime products. The preferred prime products, the light olefins, such as ethylene and propylene, are typically purified for use in derivative manufacturing processes such as polymerization processes. Therefore, in the most preferred embodiment of the recovery system, the recovery system also includes a purification system. For example, the light olefin(s) produced particularly in a MTO process are passed through a purification system that removes low levels of by-products or contaminants. Non-limiting examples of contaminants and by-products include generally polar compounds such as water, alcohols, carboxylic acids, ethers, carbon oxides, sulfur compounds such as hydrogen sulfide, carbonyl sulfides and mercaptans, ammonia and other nitrogen compounds, arsine, phosphine and chlorides. Other contaminants or by-products include hydrogen and hydrocarbons such as acetylene, methyl acetylene, propadiene, butadiene and butyne.

Other recovery systems that include purification systems, for example for the purification of olefin(s), are described in Kirk-Othmer Encyclopedia of Chemical Technology, 4th Edition, Volume 9, John Wiley & Sons, 1996, pages 249-271 and 894-899, which is herein incorporated by reference. Purification systems are also described in for example, U.S. Pat. No. 6,271,428 (purification of a diolefin hydrocarbon stream), U.S. Pat. No. 6,293,999 (separating propylene from propane), and U.S. patent application Ser. No. 09/689,363 filed Oct. 20, 2000 (purge stream using hydrating catalyst), which is herein incorporated by reference.

Typically, in converting one or more oxygenates to olefin(s) having 2 or 3 carbon atoms, an amount of hydrocarbons, particularly olefin(s), especially olefin(s) having 4 or more carbon atoms, and other by-products are formed or produced. Included in the recovery systems of the invention are reaction systems for converting the products contained within the effluent gas withdrawn from the reactor or converting those products produced as a result of the recovery system utilized.

In one embodiment, the effluent gas withdrawn from the reactor is passed through a recovery system producing one or more hydrocarbon containing stream(s), in particular, a three or more carbon atom (C3+) hydrocarbon containing stream. In this embodiment, the C3+ hydrocarbon containing stream is passed through a first fractionation zone producing a crude C3 hydrocarbon and a C4+ hydrocarbon containing stream, the C4+ hydrocarbon containing stream is passed through a second fractionation zone producing a crude C4 hydrocarbon and a C5+ hydrocarbon containing stream. The four or more carbon hydrocarbons include butenes such as butene-1 and butene-2, butadienes, saturated butanes, and isobutanes.

The effluent gas removed from a conversion process, particularly a MTO process, typically has a minor amount of hydrocarbons having 4 or more carbon atoms. The amount of hydrocarbons having 4 or more carbon atoms is typically in an amount less than 20 weight percent, preferably less than 10 weight percent, more preferably less than 5 weight percent, and most preferably less than 2 weight percent, based on the total weight of the effluent gas withdrawn from a MTO process, excluding water. In particular with a conversion process of oxygenates into olefin(s) utilizing a molecular sieve catalyst composition the resulting effluent gas typically comprises a majority of ethylene and/or propylene and a minor amount of four carbon and higher carbon number products and other by-products, excluding water.

Suitable well known reaction systems as part of the recovery system primarily take lower value products and convert them to higher value products. For example, the C4 hydrocarbons, butene-1 and butene-2 are used to make alcohols having 8 to 13 carbon atoms, and other specialty chemicals, isobutylene is used to make a gasoline additive, methyl-t-butylether, butadiene in a selective hydrogenation unit is converted into butene-1 and butene-2, and butane is useful as a fuel. Non-limiting examples of reaction systems include U.S. Pat. No. 5,955,640 (converting a four carbon product into butene-1), U.S. Pat. No. 4,774,375 (isobutane and butene-2 oligomerized to an alkylate gasoline), U.S. Pat. No. 6,049,017 (dimerization of n-butylene), U.S. Pat. Nos. 4,287,369 and 5,763,678 (carbonylation or hydroformulation of higher olefins with carbon dioxide and hydrogen making carbonyl compounds), U.S. Pat. No. 4,542,252 (multistage adiabatic process), U.S. Pat. No. 5,634,354 (olefin-hydrogen recovery), and Cosyns, J. et al., Process for Upgrading C3, C4 and C5 Olefinic Streams, Pet. & Coal, Vol. 37, No. 4 (1995) (dimerizing or oligomerizing propylene, butylene and pentylene), which are all herein fully incorporated by reference.

The preferred light olefin(s) produced by any one of the processes described above, preferably conversion processes, are high purity prime olefin(s) products that contains a single carbon number olefin in an amount greater than 80 percent, preferably greater than 90 weight percent, more preferably greater than 95 weight percent, and most preferably no less than about 99 weight percent, based on the total weight of the olefin. In one embodiment, high purity prime olefin(s) are produced in the process of the invention at rate of greater than 5 kg per day, preferably greater than 10 kg per day, more preferably greater than 20 kg per day, and most preferably greater than 50 kg per day. In another embodiment, high purity ethylene and/or high purity propylene is produced by the process of the invention at a rate greater than 4,500 kg per day, preferably greater than 100,000 kg per day, more preferably greater than 500,000 kg per day, even more preferably greater than 1,000,000 kg per day, yet even more preferably greater than 1,500,000 kg per day, still even more preferably greater than 2,000,000 kg per day, and most preferably greater than 2,500,000 kg per day.

Other conversion processes, in particular, a conversion process of an oxygenate to one or more olefin(s) in the presence of a molecular sieve catalyst composition, especially where the molecular sieve is synthesized from a silicon-, phosphorous-, and alumina-source, include those described in for example: U.S. Pat. No. 6,121,503 (making plastic with an olefin product having a paraffin to olefin weight ratio less than or equal to 0.05), U.S. Pat. No. 6,187,983 (electromagnetic energy to reaction system), PCT WO 99/18055 publishes Apr. 15, 1999 (heavy hydrocarbon in effluent gas fed to another reactor) PCT WO 01/60770 published Aug. 23, 2001 and U.S. patent application Ser. No. 09/627,634 filed Jul. 28, 2000 (high pressure), U.S. patent application Ser. No. 09/507,838 filed Feb. 22, 2000 (staged feedstock injection), and U.S. patent application Ser. No. 09/785,409 filed Feb. 16, 2001 (acetone co-fed), which are all herein fully incorporated by reference.

In an embodiment, an integrated process is directed to producing light olefin(s) from a hydrocarbon feedstock, preferably a hydrocarbon gas feedstock, more preferably methane and/or ethane. The first step in the process is passing the gaseous feedstock, preferably in combination with a water stream, to a syngas production zone to produce a synthesis gas (syngas) stream. Syngas production is well known, and typical syngas temperatures are in the range of from about 700° C. to about 1200° C. and syngas pressures are in the range of from about 2 MPa to about 100 MPa. Synthesis gas streams are produced from natural gas, petroleum liquids, and carbonaceous materials such as coal, recycled plastic, municipal waste or any other organic material, preferably synthesis gas stream is produced via steam reforming of natural gas. Generally, a heterogeneous catalyst, typically a copper based catalyst, is contacted with a synthesis gas stream, typically carbon dioxide and carbon monoxide and hydrogen to produce an alcohol, preferably methanol, often in combination with water. In one embodiment, the synthesis gas stream at a synthesis temperature in the range of from about 150° C. to about 450° C. and at a synthesis pressure in the range of from about 5 MPa to about 10 MPa is passed through a carbon oxide conversion zone to produce an oxygenate containing stream.

This oxygenate containing stream, or crude methanol, typically contains the alcohol product and various other components such as ethers, particularly dimethyl ether, ketones, aldehydes, dissolved gases such as hydrogen methane, carbon oxide and nitrogen, and fusel oil. The oxygenate containing stream, crude methanol, in the preferred embodiment is passed through well known purification processes, distillation, separation and fractionation, resulting in a purified oxygenate containing stream, for example, commercial Grade A and AA methanol. The oxygenate containing stream or purified oxygenate containing stream, optionally with one or more diluents, is contacted with one or more molecular sieve catalyst composition described above in any one of the processes described above to produce a variety of prime products, particularly light olefin(s), ethylene and/or propylene. Non-limiting examples of this integrated process is described in EP-B-0 933 345, which is herein filly incorporated by reference. In another more fully integrated process, optionally with the integrated processes described above, olefin(s) produced are directed to, in one embodiment, one or more polymerization processes for producing various polyolefins. (See for example U.S. patent application Ser. No. 09/615,376 filed Jul. 13, 2000, which is herein fully incorporated by reference.)

Polymerization processes include solution, gas phase, slurry phase and a high pressure processes, or a combination thereof. Particularly preferred is a gas phase or a slurry phase polymerization of one or more olefin(s) at least one of which is ethylene or propylene. These polymerization processes utilize a polymerization catalyst that can include any one or a combination of the molecular sieve catalysts discussed above, however, the preferred polymerization catalysts are those Ziegler-Natta, Phillips-type, metallocene, metallocene-type and advanced polymerization catalysts, and mixtures thereof. The polymers produced by the polymerization processes described above include linear low density polyethylene, elastomers, plastomers, high density polyethylene, low density polyethylene, polypropylene and polypropylene copolymers. The propylene based polymers produced by the polymerization processes include atactic polypropylene, isotactic polypropylene, syndiotactic polypropylene, and propylene random, block or impact copolymers.

In preferred embodiment, the integrated process comprises a polymerizing process of one or more olefin(s) in the presence of a polymerization catalyst system in a polymerization reactor to produce one or more polymer products, wherein the one or more olefin(s) having been made by converting an alcohol, particularly methanol, using a molecular sieve catalyst composition. The preferred polymerization process is a gas phase polymerization process and at least one of the olefins(s) is either ethylene or propylene, and preferably the polymerization catalyst system is a supported metallocene catalyst system. In this embodiment, the supported metallocene catalyst system comprises a support, a metallocene or metallocene-type compound and an activator, preferably the activator is a non-coordinating anion or alumoxane, or combination thereof, and most preferably the activator is alumoxane.

In addition to polyolefins, numerous other olefin derived products are formed from the olefin(s) recovered any one of the processes described above, particularly the conversion processes, more particularly the GTO process or MTO process. These include, but are not limited to, aldehydes, alcohols, acetic acid, linear alpha olefins, vinyl acetate, ethylene dicholoride and vinyl chloride, ethylbenzene, ethylene oxide, cumene, isopropyl alcohol, acrolein, allyl chloride, propylene oxide, acrylic acid, ethylene-propylene rubbers, and acrylonitrile, and trimers and dimers of ethylene, propylene or butylenes.

Processes and Systems for Maintaining Desired Particle Size Distributions

In a conventional OTO reaction system, a molecular sieve catalyst composition contacts an oxygenate-containing feedstock under conditions effective to convert at least a portion of the oxygenate in the oxygenate-containing feedstock to light olefins. As the feedstock contacts the molecular sieve catalyst compositions at high weight hourly space velocities and under extreme temperature and pressure conditions, a portion of the catalyst compositions can break up, e.g., attrite, to form one or more smaller attrited catalyst particles. Some catalyst attrition particles are very small in size and are referred to as catalyst fines.

As used herein, "catalyst fines" means a collection of formulated catalyst composition particles having a $d_{90}$ of no greater than 44 microns. Conversely, "catalyst non-fines" are defined herein as a collection of formulated catalyst composition particles having a $d_{90}$ of greater than 44 microns. "Catalyst coarses" is defined herein as a collection of formulated catalyst composition particles having a median particle diameter of at least 120 microns. As used herein, "catalyst non-coarses" are defined herein as a collection of formulated catalyst composition particles having a median particle diameter of less than 120 microns.

As used herein, a "median particle diameter" means the $d_{50}$ value for a specified plurality of particles. A $d_x$ particle size for purposes of this patent application and appended claims means that x percent, by volume, of a specified plurality of particles have a particle diameter no greater than the $d_x$ value. For the purposes of this definition, the particle size distribution (PSD) used to define the $d_x$ value is measured using well known laser scattering techniques using a Microtrac Model S3000 particle size analyzer from Microtrac, Inc. (Largo, Fla.). "Particle diameter" as used herein means the diameter of a specified spherical particle or the equivalent diameter of non-spherical particles as measured by laser scattering using a Microtrac Model S3000 particles size analyzer.

Due to their relatively high surface area to mass ratios, a portion of the catalyst fines in the reaction system may become undesirably entrained with the reaction effluent and exit the reaction system therewith. Catalyst fines also may become entrained with regenerator flue gas and be lost from the reaction system via the catalyst regenerator. Conversely, due to their relatively low surface area to mass ratios, larger particles such as catalyst coarses tend to be selectively retained in OTO reaction systems. The selective retention of larger particles is particularly a problem for highly attrition resistant particles.

In one embodiment, the present invention is directed to processes and systems for maintaining a desired particle size distribution in an OTO reaction system, preferably containing primary catalyst particles, by adding co-catalyst particles to the OTO reaction system, as necessary, in order to compensate for lost catalyst fines. Thus, in a preferred embodiment, the present invention is directed to a catalyst system comprising two or more catalyst compositions. For example, the catalyst system optionally comprises two catalyst compositions, one catalyst composition being more active (for example, more active for converting oxygenates to light olefins) than the other catalyst composition. In the two catalyst system according to this embodiment of the present invention, the more active catalyst composition is referred to herein as a "primary catalyst" and the less active catalyst composition is referred to as a "secondary catalyst" or a "co-catalyst." As used herein, the terms "secondary catalyst" and "co-catalyst" are synonymous and interchangeably used.

For purposes of this specification, the catalytic activity of a specified catalyst (e.g., the primary or secondary catalyst particles) is expressed in terms of the pseudo-first order rate constant, $k_{max}$. $k_{max}$ is calculated based on the peak conversion on an oxygenate to light olefin conversion profile. The greater the $k_{max}$, the more active the catalyst is for converting a specified reactant x, e.g., an oxygenate, to a product y, e.g., light olefins. When it is indicated herein that a catalyst is "active" for converting reactant x to product y, it is meant that at least some of the reactant x can be converted to product y in the presence of the catalyst.

The conditions under which $k_{max}$ is measured will depend upon the level of activity a given catalyst exhibits. It is highly desired that the maximum conversion during the measurement is controlled at or below 70 weight percent to provide more reproducible and accurate measurement results. The rates described herein refer to a pseudo-first order rate constant calculated by the following equation:

$$k_{max} = \frac{-[\ln(1-X)]}{\tau}$$

wherein X is the maximum observed conversion of a specified oxygenate feedstock, e.g., methanol, and $\tau$ is the residence time in the flow reactor in seconds, which can be calculated by multiplying oxygenate molar density at reaction conditions (in mol/cc) times the volume of active sieve (in ml) and dividing by the oxygenate molar feed rate (in mol/second). Conversion is calculated on a water and coke free basis from gas chromatographic analysis of the products and unreacted feed.

Unless otherwise specified herein, any reference to a $k_{max}$ in this specification or the appended claims refers to the activity of a catalyst (primary catalyst or co-catalyst) for converting methanol to light olefins. For the purposes of this invention, when the $k_{max}$ value for converting methanol to light olefins is discussed, dimethyl ether (DME) is considered to be equivalent to methanol. Convenient conditions for measuring the pseudo-first order rate of methanol disappearance are at 450° C., 400 WHSV and 25 psig (172 kpag) pressure in a micro-flow reactor, although other conditions may also be readily used depending upon the activity of the catalyst being employed. As used herein, the WHSV is the grams of oxygenate feed (e.g., methanol) that is fed into a reactor per hour per gram of active sieve in the reactor.

In a preferred embodiment, the present invention is directed to a process for maintaining a desired particle size distribution in a reaction system, preferably an OTO reaction system. In this embodiment, the reaction system preferably comprises a reaction zone and a disengaging zone. The process includes a step of feeding a plurality of catalyst particles, e.g., primary catalyst particles (ideally comprising molecular sieve catalyst compositions), into the reaction zone. The plurality of catalyst particles comprises catalyst fines and catalyst non-fines and has a first $k_{max}$ value for light olefins. The invention also comprises a step of contacting the plurality of catalyst particles with a feedstock, optionally comprising an oxygenate, in the reaction zone under conditions effective to convert at least a portion of the feedstock to product, optionally comprising light olefins. The product and the plurality of catalyst particles are directed from the reaction zone to the disengaging zone. An effluent stream, comprising at least a majority of the product and at least a portion of the catalyst fines, is yielded from the disengaging zone. Co-catalyst particles, having a second $k_{max}$ value less than the first $k_{max}$ value, are added to the reaction system. In various embodiments, the co-catalyst particles are added before, after and/or simultaneously with the feeding of the plurality of catalyst particles into the reaction zone. At least a majority of the catalyst non-fines are directed from the disengaging zone to the reaction zone.

In a preferred embodiment, the plurality of catalyst particles, e.g., the primary catalyst particles, has a first prime olefin selectivity ranging from about 75 weight percent to about 95 weight percent, "prime olefins" being defined as ethylene and propylene. The co-catalyst particles optionally have a second prime olefin selectivity, which preferably also ranges from about 75 weight percent to about 95 weight percent, although the conversion of methanol to light olefins may be significantly lower for the co-catalyst particles than for the primary catalyst particles, as discussed above.

A particular benefit of the present invention is that the co-catalyst particles added to the reaction system preferably are active for converting coke precursors to relatively inactive compounds. As a result, the addition of co-catalyst particles may slow the rate of formation of coke on the primary catalyst particles contained in the reaction system. This reduction in the formation in coke thereby desirably increases the lifetime of the plurality of catalyst particles, e.g., the primary catalyst particles, contained in the reaction system.

In one embodiment, the plurality of catalyst particles, e.g., the primary catalyst particles, comprise a molecular sieve composition, a binder and optionally a matrix material. The co-catalyst particles preferably comprise a matrix material, optionally a binder and/or optionally a molecular sieve composition. The co-catalyst particles optionally comprise a single component that may or may not be a molecular sieve.

Preferably, the co-catalyst particles exhibit a lower activity for converting oxygenates to light olefins than the plurality of catalyst particles (e.g., the primary catalyst particles). Such co-catalyst particles are generally easier to manufacture and are not as expensive as higher activity catalyst particles. As a result, desirable catalyst flow characteristics can be maintained in a reaction system at a relatively low cost notwithstanding the loss of catalyst fines from the reaction system due to entrained catalyst loss. In a preferred embodiment, for example, the second $k_{max}$ value for methanol conversion to light olefins is less than about 50% of the first $k_{max}$ value, preferably less than about 20% of the first $k_{max}$ value, more preferably less than about 10% of the first $k_{max}$ value, even more preferably less than about 5% of the first $k_{max}$ value, and most preferably less than about 2% of the first $k_{max}$ value, when tested under the same conditions. In terms of absolute numbers, the first $k_{max}$ value optionally is greater than about 40 Hz, preferably greater than about 80 Hz, and most preferably greater than about 150 Hz, when measured at 450° C., 400 WHSV and 25 psig (172 kPag) pressure. In the case of the co-catalyst particles, the WHSV is based on total particle weight, while for the first catalyst, the WHSV is based on the included sieve content. The second $k_{max}$ value optionally is less than about 30 Hz, preferably less than about 15 Hz, more preferably less than about 5 Hz, and most preferably less than about 2 Hz, when measured at 450° C., 400 WHSV and 25 psig (172 kPag) pressure. In one preferred embodiment, the co-catalyst is inactive for converting oxygenates to light olefins, having a second $k_{max}$ value of about 0 Hz. These relatively low $k_{max}$ values are achievable, for example, by reducing the optional sieve content in the co-catalyst particles to levels below those in the primary catalyst particles.

If the co-catalyst particles comprise a molecular sieve, then the molecular sieve optionally is selected from the group consisting of an ALPO, an all silica zeolite (e.g., the ZSM-5 analogues silicalite I and silicalite II), a dense phase crystalline aluminosilicate, SAPO-5, SAPO-8, SAPO-11, SAPO-16, SAPO-17, SAPO-18, SAPO-20, SAPO-31, SAPO-34, SAPO-35, SAPO-36, SAPO-37, SAPO-40, SAPO-41, SAPO-42, SAPO-44, SAPO-47, SAPO-56, AEI/CHA intergrowths, metal containing forms thereof, intergrown forms thereof, and mixtures thereof. The fraction of sieve contained in the co-catalyst particles will typically be lower than that contained in the primary catalyst particles. As used herein, a "dense phase crystalline aluminosilicate" means an aluminosilicate having a framework density (the number of tetrahedrally coordinated T-atoms per 1000 Å$^3$) larger than 21. See Baerlocher, C H., Meier, W. M., Olson, D. H., "Atlas of Zeolite Framework Types," 5th Revised Edition, pp. 3-4 (2001), the entirety of which is incorporated herein by reference.

Additionally or alternatively, the plurality of catalyst particles, e.g., the primary catalyst particles, comprise a molecular sieve selected from the same group of molecular sieves recited above. Optionally, the primary catalyst particles and/or the co-catalyst particles comprise one or more of silica, alumina, aluminosilicates, clay and mixtures thereof.

The relative flow rate of the co-catalyst particles that are directed from the storage vessel to the reaction system will depend on various parameters such as the particle size distribution of the total catalyst particles in the reaction system, the relative attrition index of the co-catalyst particles and the primary catalyst particles, the particle size distribution of the co-catalyst particles to be added, reaction conditions, reactor diameter, efficiency of particle retention in the reactor effected by cyclones and the like, the addition rate of primary catalyst particles optionally added to the reaction system and the characteristics of such primary catalyst particles, and the target equilibrium inventory fines level desired. This flow rate of co-catalyst particles is described as a make up rate and ideally is adjusted such that the fines content of the thus admitted co-catalyst particles will approximately match the rate of loss of similarly sized particles from the reaction system. Thus, in this case, the total fines content comprising primary catalyst and co-catalyst particles contained in the reaction system will advantageously remain essentially constant. It is contemplated, however, that particularly small fines, e.g., on the order of from about 1 to about 2 microns, that are lost might not be replaced with similarly-sized co-catalyst particles because such co-catalyst particles would likely immediately exit the reaction system due to entrained catalyst loss.

The fraction of co-catalyst particles in ensemble of the primary catalyst particles plus co-catalyst particles in the reaction system preferably is on the order of from about 1 to about 20 wt. %, more preferably from about 1 to about 10 wt. %, and most preferably from about 1 to about 5 wt %. Typically, the fraction of primary catalyst in the reaction system will be very high, approaching 100 wt. %, during reactor start-up as the catalyst particles in the reaction system are entirely primary catalyst particles. As the primary catalyst particles attrite and co-catalyst is added to the reaction system according to the present invention, the weight ratio of primary catalyst particles to co-catalyst particles in the reaction system will be reduced and eventually stabilize to a desired target fraction determined from the relative attrition resistance of the primary and co-catalyst particles and the retention efficiency of the cyclones. At steady loss rates, the fraction of co-catalyst particles will eventually stabilize to a nearly constant value that is referred to as steady state. Thus, it should be understood that during reactor start-up, the plurality of catalyst particles contained in the reaction system may initially comprise virtually entirely primary catalyst particles; however, as co-catalyst particles are added to the reaction system, the plurality of catalyst particles contained in the reaction system will comprise both primary catalyst particles and co-catalyst particles.

In one embodiment, both primary catalyst particles and co-catalyst particles are added to the reaction system to make up for lost catalyst fines. For example, in one embodiment, when the co-catalyst particles have a particle size distribution range spanning a $d_2$ of about 20 microns and a $d_{90}$ of about 44 microns and the co-catalyst particles have approximately the same attrition index as the primary catalyst particles, the addition flow rate of the co-catalyst particles is from about 5 wt % to about 100 wt % of the addition flow rate of the primary catalyst particles, more preferably from about 10 wt % to about 80 wt % of the addition flow rate of the primary catalyst particles, and most preferably from about 20 wt % to about 50 wt % of the addition flow rate of the primary catalyst particles when the equilibrium inventory fines level in the reaction system is targeted to contain at least 10 wt % fines with a particle diameter less than 44 microns.

In one embodiment, the plurality of catalyst particles has a first median particle diameter and the co-catalyst particles have a second median particle diameter, which is less than the first median particle diameter. The co-catalyst particles optionally have a median particle diameter of less than about 50 microns and preferably less than about 40 microns. By directing relatively small co-catalyst particles to the reaction system, the flow characteristics of the catalyst particles contained in the reaction system can be desirably maintained at desirable conditions notwithstanding the loss of catalyst fines from the reaction system due to entrained catalyst loss. Higher median particle diameters are desired for the co-catalyst particles, e.g., greater than 40 microns, when the attrition index of the co-catalyst particles is greater than that of the primary catalyst particles.

In this invention, attrition resistance of the plurality of catalyst particles and of the co-catalyst particles is measured using an Attrition Rate Index (ARI). The ARI is used over other measurement methods, since many other methods are not sufficient to measure very highly attrition resistant molecular sieve catalyst particles, which may be implemented according to the present invention.

The ARI methodology is similar to the conventional Davison Index method. The smaller the ARI, the more resistant to attrition, hence the harder the catalyst. The ARI is measured by adding 6.0±0.1 g of catalyst that has been screened to pass through a 120 mesh US standard sieve (screen opening of 125 microns) but retained on a No. 270 US standard screen size (screen opening of 53 microns). This is conventionally described as "−120/+270" and is used as such herein. Approximately 23,700 scc/min of nitrogen gas is bubbled through a water-containing bubbler to humidify the nitrogen. The wet nitrogen passes through an attrition cup, and exits the attrition apparatus through a porous fiber thimble. The flowing nitrogen removes the finer particles, with the larger particles being retained in the cup. The porous fiber thimble separates the fine catalyst particles from the nitrogen that exits through the thimble. The fine particles remaining in the thimble represent catalyst that has broken apart through attrition.

The nitrogen flow passing through the attrition cup is maintained for 1 hour. The fines collected in the thimble are removed from the unit. A new thimble is then installed. The catalyst left in the attrition unit is attrited for an additional 3 hours, under the same gas flow and moisture levels. The fines collected in the thimble are recovered. The collection of fine catalyst particles separated by the thimble after the first hour are weighed. The amount in grams of fine particles divided by the original amount of catalyst charged to the attrition cup expressed on per hour basis is the ARI, in wt %/hr (higher ARI values correspond with higher rates of attrition). Thus, the calculation of the ARI may be expressed as follows:

$$ARI = \frac{\left[\frac{C}{(B+C)}\right]}{D} \cdot 100$$

wherein,
B=weight of catalyst left in the cup after the attrition test;
C=weight of collected fine catalyst particles after the first hour of attrition treatment; and
D=duration of treatment in hours after the first hour attrition treatment.

In one embodiment of the present invention, the ARI of both the primary catalyst particles and the co-catalyst particles ranges from about 0.01 to about 2.0 weight percent per hour, preferably from about 0.01 to about 1.0 weight percent per hour, and most preferably from about 0.01 to about 0.5 weight percent per hour. In one embodiment, the plurality of catalyst particles (e.g., the primary catalyst particles) has a first ARI, and the co-catalyst particles have a second ARI, and the ratio of the second ARI to the first ARI is from about 0.1 to about 1000, preferably from about 1 to about 1000, more preferably from about 1 to about 100, and most preferably from about 1 to about 10. Optionally, the co-catalyst particles attrite more readily than the plurality of catalyst particles. In this embodiment, the ratio of the second ARI to the first ARI preferably is greater than about 0.1 and less than 1. In one embodiment, the plurality of catalyst particles (e.g., primary catalyst particles) has an ARI of from about 0.01 weight percent per hour to about 2.0 weight percent per hour, preferably from about 0.01 weight percent per hour to about 1.0 weight percent per hour.

In one preferred embodiment, the co-catalyst particles comprise a molecular sieve, hydrotalcite and a rare earth metal component. A basic oxide may be substituted for hydrotalcite. Alternatively, the co-catalyst particles comprise a basic oxide or hydrotalcite, and optionally a rare earth metal component, but does not comprise a molecular sieve. In another preferred embodiment, clay and an inorganic oxide binder are combined to produce a particle having very low catalytic activity for oxygenate conversion.

In yet another embodiment, the co-catalyst particles comprise a component selected from the group consisting of: silica, alumina, aluminosilicates, clay and mixtures thereof.

Co-catalyst particles comprising hydrotalcite, optionally with a rare earth metal, provide some catalyst benefits to the primary catalyst particles, such as reducing the coke yield on the primary catalyst particles when used in oxygenate conversion reactions. Hydrotalcites are naturally occurring, porous, crystalline mixed metal Mg—Al oxide materials with an empirical formula of $Mg_6Al_2(CO_3)(OH)_{16} \cdot 4(H_2O)$. As a result, the materials have basic properties and can catalyze basic hydrocarbon transformations. Hydrotalcites are commercially available from Sasol/Condea (Pural M G) and from Tricat Zeolites GmbH. One of the main advantages of incorporating hydrotalcites into the co-catalyst particles is that the material does not have to retain its crystalline nature after calcination in order to retain its catalyst performance as a co-catalyst. The use of hydrotalcites in molecular sieve catalyst compositions is described in U.S. patent application Ser. No. 10/634,557, filed Aug. 6, 2003, the entirety of which is incorporated herein by reference. See also U.S. Pat. No. 6,010,619, the entirety of which is incorporated herein by reference. In one embodiment the co-catalyst particles comprise MgO.

The invention optionally further comprises a step of monitoring the particle size distribution of the catalyst particles (preferably including primary and co-catalyst particles) contained in the reaction system. Ideally, the monitoring comprises monitoring a specific $d_x$ value or values, e.g., the $d_{50}$ value, for the catalyst particles contained in the reaction system. The monitoring preferably is performed by a laser scattering particle size analyzer such as a Microtrac Model S3000 Particle Size Analyzer from Microtrac, Inc. (Largo, Fla.). The monitoring may occur either online or offline. In this embodiment, the step of directing the co-catalyst particles to the fluidized reactor optionally is responsive to a determination in the monitoring step that the specified $d_x$ value has exceeded a predetermined limit. The predetermined limit may vary widely depending on the $d_x$ value that is monitored, but for $d_{50}$ preferably is greater than 120 microns, between about 100 and about 120 microns, or between about 90 and about 100 microns. Optionally, the monitoring is performed by a laser scattering particle size analyzer, a Coulter counter, device for determining rate of sedimentation, or a mechanical screening device. By monitoring the particle size distribution of the catalyst particles contained in the reaction system, co-catalyst particles can be added as needed in order to maintain consistent fluidization characteristics in the reaction system over time.

Catalyst fluidization can be expressed in terms of a fluidization index, which is defined herein by the following formula:

$$FI = \frac{e^{0.00508 \cdot f}}{d^{0.586} \cdot den^{0.663}}$$

wherein,

FI=Fluidization Index;

f=weight percent of 0-40 micron fines, based on the total catalyst population;

d=surface-volume diameter in microns; and den=average bulk density (g/cc).

See Raterman, M., "FCC Catalyst Flow-Problem Predictions," *Oil & Gas Journal*, Jan. 7, 1985, the entirety of which is incorporated herein by reference.

The fluidization index is used in conjunction with historical data specific to a particular unit to forecast ease or difficulty of circulation in the unit as catalyst properties change. A minimum acceptable fluidization index may be established from historical data and steps taken to ensure that fluidization index does not fall below the minimum. The minimum value is unit specific because of variations in design (e.g. U-bend, J-bend, aeration patterns, etc.). Some exemplary non-limiting values of fluidization indexes are shown in Table I, below, as a function of catalyst properties.

TABLE I

Exemplary Fluidization Indexes for Several Catalyst Characteristics

| den, g/cc | f, wt. % 0–40 micron | d, microns | FI | % change |
|---|---|---|---|---|
| 0.74 | 1 | 74 | 0.106459 | −4.3 |
| 0.74 | 5 | 71 | 0.111228 | "Minimum" |
| 0.74 | 10 | 68 | 0.116922 | 5.1 |
| 0.74 | 12 | 67 | 0.119114 | 7.1 |

Using a hypothetical case (5 weight percent 0-40 microns) as the minimum value, it may be seen that operating at 1 weight percent fines reduces the fluidization index by 4.3 percent below the minimum value which would likely result in circulation problems. Increasing the fines to 10 weight percent raises the fluidization index by 5.1 percent over the minimum value, which would improve circulation in the unit. In general, this can be carried over to operation of fluidized beds (regenerator, stripper, catalyst cooler) where higher fluidization values would give smoother fluidization with reduced by-passing of gas.

In one embodiment, the present invention is directed to a process for maintaining desirable fluidization characteristics in a reactor. In this embodiment, the process includes the step of providing a first plurality of catalyst particles in a reactor, wherein the first plurality of catalyst particles comprises catalyst fines and catalyst non-fines and has a first fluidization index. A product and a portion of the catalyst fines are yielded from the reactor to form a second plurality of catalyst particles in the reactor, wherein the second plurality of catalyst particles has a second fluidization index less than the first fluidization index. Co-catalyst particles are added to the reaction system to form a third plurality of catalyst particles in the reactor, wherein the third plurality of catalyst particles has a third fluidization index greater than the second fluidization index. Thus, the first plurality of catalyst particles has a first median particle diameter, and the co-catalyst particles have a second median particle diameter, which preferably is less than the first median particle diameter.

In another embodiment, the invention is directed to a process for maintaining a specifically defined particle size distribution in a reaction system. In this process, the invention includes a step of feeding a plurality of catalyst particles into a reaction zone. The plurality of catalyst particles has a $d_2$ of at least about 7 microns (preferably at least about 20 microns), a $d_{10}$ of less than about 45 microns, a $d_{50}$ between about 75 and about 100 microns (preferably between about 75 and about 90 microns), and a $d_{90}$ of less than about 150 microns (preferably less than about 120 microns). The plurality of catalyst particles contacts a feedstock in the reaction zone under conditions effective to convert at least a portion of the feedstock to product. The product and the plurality of catalyst particles are directed to a disengaging zone. The product and a portion of catalyst fines are yielded from the disengaging zone under conditions effective to increase one or more of the $d_2$, the $d_{10}$, the $d_{50}$ and the $d_{90}$ to provide an increased $d_2$, an increased $d_{10}$, an increased $d_{50}$ or an increased $d_{90}$. One or more of the increased $d_2$, the increased $d_{10}$, the increased $d_{50}$ or the increased $d_{90}$ are then decreased by adding co-catalyst particles to the reaction system. Thus, the co-catalyst particles preferably have a second median particle diameter, which is less than the $d_{50}$.

In a similar embodiment, the invention is to a process that includes a step of providing a plurality of catalyst particles in a reaction zone, wherein the plurality of catalyst particles has a $d_2$ of at least about 7 microns, a first median particle diameter (preferably between about 75 microns and about 90 microns), and a $d_{90}$ of less than about 150 microns (preferably no greater than about 120 microns). The plurality of catalyst particles comprises primary catalyst particles. The primary catalyst particles contact a feedstock, preferably an oxygenate such as methanol, in the reaction zone under conditions effective to convert at least a portion of the feedstock to product, e.g., light olefins. The product and the plurality of catalyst particles are directed to a disengaging zone. The first median particle diameter is increased to a second median particle diameter by yielding or losing a portion of catalyst fines from the disengaging zone. The second median particle diameter is decreased to a third median particle diameter by adding co-catalyst particles to the reaction system. In this embodiment, the co-catalyst particles optionally have a fourth median particle diameter, which is less than the first median particle diameter. Preferably, the fourth median particle diameter is less than about 50 microns, preferably less than about 40 microns.

The FIGURE illustrates one embodiment of the present invention. As shown, an oxygenate such as methanol is directed through lines 100 to OTO fluidized reactors 102 (two are shown). The fluidized reactors 102 form a reaction zone in which the oxygenate contacts primary catalyst particles under conditions effective to convert the oxygenate to light olefins and various by-products, which are yielded from the fluidized reactors 102 into a disengaging zone 109. The disengaging zone 109 is adapted to separate the primary catalyst particles from the products of the OTO reaction process with cyclone separators (not shown) or other separation devices, which are well-known in the art. As shown, an olefin-containing stream is yielded from the disengaging zone 109 in line 104. The olefin-containing stream in line 104 optionally comprises methane, ethylene, ethane, propylene, propane, various oxygenate byproducts, C4+ olefins, water and hydrocarbon components. Additionally, olefin-containing stream 104 may comprise a minor amount of entrained catalyst fines. The olefin-containing stream in line 104 is then directed to a separation sequence, not shown, in order to separate the desired components, e.g., the light olefins, from the olefin-containing stream. The primary catalyst particles that are separated from the olefin product are directed by gravity to a collection zone 111 or a plurality of collection zones, which direct the catalyst particles to one or more standpipes. As shown, catalyst particles are collected in collection zone 111 and directed to a single standpipe 112, which directs the catalyst particles back to the fluidized reactors 102. In other preferred embodiments, not shown, the collection zone 111 directs the catalyst particles back to the fluidized reactors 102 via a plurality of standpipes, each of which preferably directs the catalyst particles to a respective fluidized reactor.

The FIGURE also illustrates a catalyst regeneration system, which is in fluid communication with fluidized reactor 102. As shown, at least a portion of the catalyst compositions contained in disengaging zone 109 is withdrawn and transported, preferably in a fluidized manner, in conduit 133 from the disengaging zone 109 to a catalyst stripper 134. In the catalyst stripper 134, the catalyst compositions contact a stripping medium, e.g., steam and/or nitrogen, under conditions effective to remove interstitial hydrocarbons from the molecular sieve catalyst compositions. As shown, stripping medium is introduced into catalyst stripper 134 through line 135, and the resulting stripped stream 136 is released from catalyst stripper 134. Optionally, all or a portion of stripped stream 136 is directed back to one or more of the disengaging zone 109, the standpipe(s) 111 or the fluidized reactor 102.

During contacting of the oxygenate feedstock with the molecular sieve catalyst composition in the fluidized reactor 102, the molecular sieve catalyst composition may become at least partially deactivated. That is, the molecular sieve catalyst composition becomes at least partially coked. In order to reactivate the molecular sieve catalyst composition, the catalyst composition preferably is directed to a catalyst regenerator 138. As shown, the stripped catalyst composition is transported, preferably in the fluidized manner, from catalyst stripper 134 to catalyst regenerator 138 in conduit 137. Preferably, the stripped catalyst composition is transported in a fluidized manner through conduit 137.

In catalyst regenerator 138, the stripped catalyst composition contacts a regeneration medium, preferably comprising oxygen, under conditions effective (preferably including heating the coked catalyst) to at least partially regenerate the catalyst composition contained therein. As shown, the regeneration medium is introduced into the catalyst regenerator 138 through line 139, and the resulting regenerated catalyst compositions are transported, preferably in a fluidized meaner, from catalyst regenerator 138 back to the disengaging zone 109 through conduit 141. Ultimately, the regenerated catalysts are reintroduced into the fluidized reactors 102. The gaseous combustion products are released from the catalyst regenerator 138 through flue gas stream 140 after separation from the catalyst particles with cyclone separators (not shown) or other separation devices. Flue gas stream 140 also may comprise a minor amount of entrained catalyst fines. In another embodiment, not shown, the regenerated catalyst composition additionally or alternatively is directed, optionally in a fluidized manner, from the catalyst regenerator 138 to one or more of the fluidized reactor 102 and/or the catalyst stripper 134. In one embodiment, not shown, a portion of the catalyst composition in the reaction system is transported directly, e.g., without first passing through the catalyst stripper 134, optionally in a fluidized manner, from the fluidized reactor 102 to the catalyst regenerator 138.

As the catalyst compositions contact the regeneration medium in catalyst regenerator 138, the temperature of the catalyst composition may increase due to the exothermic nature of the regeneration process. As a result, it may be desirable to control the temperature of the catalyst composition by directing at least a portion of the catalyst composition from the catalyst regenerator 138 to a catalyst cooler 143. As shown, the catalyst composition is transported in a fluidized manner from catalyst regenerator 138 to the catalyst cooler 143 through conduit 142. The resulting cooled catalyst composition is transported, preferably in a fluidized manner from catalyst cooler 143 back to the catalyst regenerator 138 through conduit 144. In another embodiment, not shown, the cooled catalyst composition additionally or alternatively is directed, optionally in a fluidized manner, from the catalyst cooler 143 to one or more of the fluidized reactor 102 and/or the catalyst stripper 134.

In order to compensate for lost catalyst fines and maintain desired fluidization and hydrodynamic characteristics in the reaction system, according to the present invention, co-catalyst particles are added to the reaction system. As shown, co-catalyst particles 105 are stored in storage vessel 106. Optionally, the co-catalyst particles are blanketed with a blanketing medium such as nitrogen or argon, which is introduced through line 110. Typically, however, it is not necessary to blanket the co-catalyst particles, particularly if the co-catalyst particles are not active for converting oxygenates to light olefins.

As needed, co-catalyst particles 105 are withdrawn from the storage vessel 106 and are transported, preferably in a fluidized manner, in line 107 to the fluidized reactor 102. Flow control device 108, such as a valve, controls the flow of co-catalyst particles from the storage vessel 106 to the reaction system. As shown, the co-catalyst particles are directed from the storage vessel 106 to the disengaging zone of fluidized reactor 102. In other embodiments, however, the co-catalyst particles are directed to the reaction zone, e.g., to the riser reactors, of the fluidized reactor 102 and/or to the one or more components of the regeneration system. For example, the co-catalyst particles optionally are introduced into one or more of lines 133, 135, 137, 142, 144 and/or 141. Optionally, the co-catalyst particles are introduced directly into the catalyst stripper 134, the catalyst cooler 143, and/or the catalyst regenerator 138. By introducing co-catalyst particles 105 into the reaction system, improved fluidization and circulation properties can be advantageously realized in the fluidized reactors 102, the disengaging zone 109, the collection zone 111, the standpipe 112, the catalyst stripper 134, the catalyst regenerator 138, the catalyst cooler 143, as well as in one or more of lines 133, 137, 141, 142 and 144.

Additionally, primary catalyst particles optionally are added to the reaction system through line 101, which, as shown, introduces primary catalyst particles to the catalyst regenerator 138. In other embodiments, primary catalyst particles are added to one or more of the disengaging zone 109, the fluidized reactors 102, or to other regions of the regeneration zone, e.g., to the catalyst stripper 134, the catalyst cooler 143, and/or one or more of lines 133, 135, 137, 142, 144 and/or 141.

In one embodiment, the co-catalyst particles are directed to and admixed with the primary catalyst particles prior to introduction into the reaction system. For example, the primary catalyst particles and co-catalyst particles optionally are admixed and introduced into the reaction system via line 101. In another embodiment, the thusly admixed primary catalyst particles and co-catalyst particles are introduced into one or more of lines 133, 135, 137, 142, 144 and/or 141. Optionally, the admixed catalyst particles are introduced directly into the catalyst stripper 134, the catalyst cooler 143, and/or the catalyst regenerator 138.

Preferred Particle Size Distributions

In a related embodiment, the invention is directed to a plurality of catalyst particles having a specific particle size distribution. In this embodiment the particle size distribution comprises: (a) a $d_2$ of at least about 7 microns (preferably at least about 20 microns); (b) a $d_{10}$ of less than about 45 microns; (c) a $d_{50}$ between about 75 and about 100 microns; and (d) a $d_{90}$ of no greater than about 150 microns. It has been discovered that the specified particle size distribution provides highly desirably fluidization characteristics in OTO reaction systems.

In a more preferred embodiment, the particle size distribution comprises: (a) a $d_2$ of at least about 7 microns; (b) a $d_{10}$ of less than about 45 microns; (c) a $d_{50}$ between about 75 and 90 microns; and (d) a $d_{90}$ of no greater than about 120 microns.

In another preferred embodiment, the particle size distribution comprises: (a) a $d_2$ of at least about 20 microns; (b) a $d_{10}$ of from about 40 to about 50 microns; (c) a $d_{50}$ of from about 70 to about 80 microns; (d) a $d_{75}$ of from about 90 to about 100 microns; and (e) a $d_{90}$ of less than about 130 microns. In simulation studies, this particle size distribution, containing about 10 weight percent fines, based on the total solids weight in the reaction system, performed particularly well having highly desirable fluidization characteristics.

In these embodiments, the plurality of catalyst particles preferably comprise primary catalyst particles and co-catalyst particles. The primary catalyst particles have a first median particle diameter, and the co-catalyst particles have a second median particle diameter, which preferably is less than the first median particle diameter. The primary catalyst particles preferably comprise a molecular sieve selected from the group consisting of SAPO-5, SAPO-8, SAPO-11, SAPO-16, SAPO-17, SAPO-18, SAPO-20, SAPO-31, SAPO-34, SAPO-35, SAPO-36, SAPO-37, SAPO-40, SAPO-41, SAPO-42, SAPO-44, SAPO-47, SAPO-56, AEI/CHA intergrowths, metal containing forms thereof, intergrown forms thereof, and mixtures thereof. The co-catalyst particles optionally comprise a molecular sieve selected from the group consisting of an ALPO, an all silica zeolite, a dense phase crystalline aluminosilicate, SAPO-5, SAPO-8, SAPO-11, SAPO-16, SAPO-17, SAPO-18, SAPO-20, SAPO-31, SAPO-34, SAPO-35, SAPO-36, SAPO-37, SAPO-40, SAPO-41, SAPO-42, SAPO-44, SAPO-47, SAPO-56, AEI/CHA intergrowths, metal containing forms thereof, intergrown forms thereof, and mixtures thereof. As described in detail above, the primary catalyst particles have a first $k_{max}$ value and the co-catalyst particles have a second $k_{max}$ value, which is less than the first $k_{max}$ value.

Optionally, the co-catalyst particles will not contain any molecular sieve component. In this embodiment, the co-catalyst particles optionally comprise a component selected from the group consisting of: inorganic oxides (such as alumina and/or silica), a clay or clays, and mixtures thereof. Thus, the component optionally is selected from the group consisting of silica, alumina, aluminosilicates, clay and mixtures thereof. In yet another molecular sieve-free embodiment, the co-catalyst particles comprise one or more of the following: hydrotalcite, a basic oxide, a rare earth element, an inorganic oxide and/or clay.

Improved Catalyst Regeneration

It has now been discovered that poor fluidization in dense-bed catalyst regenerators is detrimental to unit operations in general and catalyst regeneration in particular. Poor fluidization in the dense bed of the regenerator disrupts solids flow from the reactor side into the regenerator and out of the regenerator and back to the reactor. Consequently, poor fluidization in the regenerator can propagate and upset the entire circulating fluid bed process.

Poor fluidization in catalyst regenerators occurs due to insufficient fines in the solids inventory and introducing excessively high amounts of vapor, e.g., air, into the regenerator. Both factors severely disrupt the proper fluidization of catalyst regenerators and have similar detrimental consequences. Specifically, carbon monoxide levels in the flue gas from the regenerator increase during periods of poor fluidization because such unstable operations increase the probability of carbon monoxide channeling though the bed without being oxidized to carbon dioxide. These increased carbon monoxide levels are a problem both environmentally due to undesired emissions and operationally due to afterburning, described below. Also, the burning of coke off of the catalyst tends to be less efficient during periods of poor fluidization as more air is needed per gram of carbon removed from the catalyst. Poor fluidization also increases the probability that catalyst will pass through the regenerator without being fully regenerated (solids by-passing) or unnecessarily subjected to hydrothermal stress and possible damage due to being held-up in a hydrodynamic dead-zone ("caught" in the regenerator) resulting in significantly longer residence times in the regenerator than the average residence time in the regenerator. Proper fluidization of the catalyst regenerator improves its efficiency, lowers emissions, disrupts the unit less, and protects the catalyst from undesired hydrothermal stresses.

Catalyst in continuous fluid-bed processes such as the OTO reaction process are regenerated by being delivered to a high-temperature fluid-bed catalyst regenerator where the coke is burned off using a regeneration medium, which preferably is selected from the group consisting of $O_2$, $O_3$, $SO_3$, $N_2O$, NO, $NO_2$, $N_2O_5$, air, air diluted with nitrogen or carbon dioxide, oxygen and water, carbon monoxide and hydrogen. During combustion of coke, the carbonaceous species comprising coke typically burns to form carbon monoxide. Typically, the carbon monoxide is subsequently oxidized in the vapor phase forming more benign carbon dioxide and releasing a considerable amount of heat. If the carbon monoxide is oxidized in the vapor phase associated with a dense phase of catalyst in the fluid bed the heat of combustion is absorbed by the nearby solids and operations are smooth. If the carbon monoxide manages to channel from the dense-phase region into a region lean in solids and then oxidize, the heat of combustion produces localized hot spots that are disruptive to unit operations; this phenomenon is colloquially referred to as "afterburning."

In order to ensure low levels of carbon monoxide in the flue gas leaving the regenerator and to stabilize operations by reducing the occurrences of afterburning, combustion promoters are added as co-catalyst to the solids inventory circulating through the unit. Addition of combustion promoting co-catalyst greatly enhances the probability that the carbon monoxide is oxidized in a dense phase region as opposed to detrimentally oxidizing in a lean phase region. In one embodiment, about 1 weight percent platinum (or other Group VIII transition metal) supported on alumina oxide combustion promoting co-catalyst is added to the reaction system, based on the total weight of the combustion promoting co-catalyst added to the reaction system, in order to control afterburning.

Preferred combustion promoting co-catalysts are commercially available through Intercat Inc. (Sea Girt, N.J.) under trade names such as COP-850, COP-550, COP-375, COP-Blue, PC-500, COP-250, COP-500s, and CATNA480. In one embodiment, the combustion promoting co-catalyst is added to the reaction system to provide from about 0.001 to about 5 weight percent, preferably from about 0.01 to about 1 weight percent, more preferably from about 0.05 to about 0.5 weight percent combustion promoting co-catalyst in the reaction system, based on the total weight of the solids inventory in the reaction system. The amount of the combustion promoting metal on the combustion promoting co-catalyst preferably ranges from about 0.1 to about 10 weight percent, more preferably from about 0.5 to about 3 weight percent, and most preferably about 1 weight percent, based on the total weight of the combustion promoting co-catalyst added to the reaction system. Optionally, fresh combustion promoting co-catalyst is repeatedly added to the reaction system, say on the order of once every 3-14 days, preferably about every 3-8 days. The need for the combustion promoting co-catalyst is determined by increased frequency of afterburning episodes or by rising CO levels in the regenerator flue gas. The need for adding a Group VIII metal on alumina combustion promoting co-catalyst may be reduced as the average age of the catalyst (amount of time it has spent in the process) increases due to the accumulation of metals such as iron, which also promote combustion of carbon monoxide.

Catalytic combustion of carbon monoxide is a structure-insensitive reaction (the reaction rate per exposed metal atom is fairly independent of particle size of or the crystal face of the metal catalyzing the reaction) and is preferably catalyzed by Group VIII transition metals (Groups 8, 9 and 10 in the IUPAC system), specifically, a metal selected from the group consisting of iron, cobalt, nickel, ruthenium, rhodium, palladium, osmium, iridium and platinum. However, other transition metals such as gold, silver or copper may be used. See, for example, PCT published application WO2004/014793 A1, the entirety of which is incorporated herein by reference. Since it is only the atoms at the surface of a metal particle that participate in the catalytic combustion of carbon monoxide, the Group VIII metals are preferably dispersed on an inert carrier such as alumina in order to maximize the efficiency with which a mass of metal is used in the reaction. The inert carrier does not play a significant role in promoting the combustion of carbon monoxide and therefore can be any fairly inert, typically porous, solid that catalytic Group VIII metal can be bound to. A non-limiting list of exemplary inert carriers comprises clays, magnesia, titania, zeolites, and/or hydrotalcites.

Group VIII metals which are active for carbon monoxide combustion may be impregnated on the fines which are added to the solid inventory of a fluid-bed system in order to improve fluidization. Consequently, such impregnated fines can serve two functions: (1) improving the hydrodynamics of the system; and (2) helping manage the combustion of carbon monoxide. The metal can be introduced to the fines through any of the techniques known to those skilled in the art (such as incipient wetness followed by calcination and reduction) or prepared in a manner similar to the commercial combustion promoter COP-850. Since the reaction is structure-insensitive, the small size of the fines impregnated with combustion promoter is not anticipated to have any deleterious effects on the metals ability to promote the oxidation of carbon monoxide.

Iron is one of the least expensive of the Group VIII metals and therefore is an attractive candidate for promoting carbon monoxide combustion. In test reactors, iron has been observed to accumulate on OTO catalyst with increasing time-on-stream. It is believed that the iron deposition on the catalyst in test reactors comes from the erosion of the stainless steel walls thereof and through accumulation in the oxygenate feed. Thus, the need for platinum (or other Group VIII metal) on alumina combustion promoting co-catalyst in OTO reaction systems will be less and less as the average time-on-stream of the catalyst in the reaction system increases because the iron content of the OTO-catalyst (e.g. the primary catalyst) increases and serves as a combustion promoter.

In another embodiment, iron is intentionally added to the solids inventory of an OTO reaction system, e.g., as the co-catalyst, in order to promote carbon monoxide combustion in the catalyst regenerator. Optionally, iron (or another Group VIII metal) is added to the catalyst fines, which may be added to improve the fluidization of the circulating fluid bed system. Additionally or alternatively, the iron is added to any of the three main components of the catalyst matrix (the clay, the binder, or, to an active molecular sieve (e.g., SAPO-34)). Adding the iron to the molecular sieve may be detrimental to catalyst function and adding iron to the binder may be impractical. Preferably, the clay used as the catalyst matrix material is specifically selected for its relatively high iron content in order to promote carbon monoxide combustion while it is in the catalyst regenerator.

In one embodiment, the iron is added to the matrix material using methods known to those skilled in the art (such as ion exchange) or left in the clay by skipping any steps taken to remove it. Most natural clays have quite high iron contents, e.g., on the order of a few thousand wppm or more, and the specification of iron content in the clay used for the catalyst formulation may be altered (raised) for the benefit of carbon monoxide combustion. Another manner in which iron could be introduced into the OTO catalyst so that it can promote CO combustion in the regenerator is to specify/allow a minimum iron content in the OTO feed (preferably methanol). Iron in the feed would accumulate in the catalyst matrix until a saturation point and could assure a substantial quantity of iron available for promotion of CO combustion.

Thus, in one embodiment, the feedstock comprises a regeneration medium and the product comprises combustion products. The co-catalyst particles may enhance combustion of coke from the plurality of catalyst particles, for example, by improving fluidization in the regeneration system. Optionally, the particle size distribution of the co-catalyst particles compensate for lost catalyst fines, as described in detail above, in order to facilitate catalyst fluidization in the reaction system. Additionally or alternatively, the co-catalyst particles enhance the combustion of carbon monoxide to carbon dioxide to a greater extent than the primary catalyst particles. In this embodiment, the co-catalyst particles preferably comprise a combustion enhancing metal selected from the group consisting of: iron, cobalt, nickel, ruthenium, rhodium, palladium, osmium, iridium and platinum. Thus, in one embodiment, the invention provides for maintaining desirable fluidization and flow characteristics in an OTO reaction system while also enhancing catalyst regeneration characteristics.

While the present invention has been described and illustrated by reference to particular embodiments, those of ordinary skill in the art will appreciate that the invention lends itself to variations not necessarily illustrated herein. For this reason, then, reference should be made solely to the appended claims for purposes of determining the true scope of the present invention.

We claim:

1. A process for maintaining a particle size distribution in a reaction system, wherein the process comprises the steps of:
    (a) feeding a plurality of catalyst particles into a reaction zone, wherein the plurality of catalyst particles has a first median particle diameter, a $d_2$ of at least about 7 microns, a $d_{10}$ of less than about 45 microns, a $d_{50}$ between about 75 and about 100 microns, and a $d_{90}$ of less than about 150 microns;
    (b) contacting the plurality of catalyst particles with a feedstock in the reaction zone under conditions effective to convert at least a portion of the feedstock to product;
    (c) directing the product and at least a portion of the plurality of catalyst particles to a disengaging zone;
    (d) yielding the product and a portion of catalyst fines from the disengaging zone under conditions effective to increase one or more of the $d_2$, the $d_{10}$, the $d_{50}$ and the $d_{90}$ to provide an increased $d_2$, an increased $d_{10}$, an increased $d_{50}$ or an increased $d_{90}$; and
    (e) decreasing one or more of the increased $d_2$, the increased $d_{10}$, the increased $d_{50}$ or the increased $d_{90}$ by adding co-catalyst particles to the reaction system.

2. tie process of claim 1, wherein the $d_{50}$ is between about 75 and about 90 microns, and the $d_{90}$ is less than about 120 microns.

3. The process of claim 1, wherein the feedstock comprises a regeneration medium and the product comprises combustion products, and wherein the co-catalyst particles enhance combustion of coke from the plurality of catalyst particles.

4. The process of claim 3, wherein the co-catalyst particles comprise a metal selected from the group consisting of: iron, cobalt, nickel, ruthenium, rhodium, palladium, osmium, iridium and platinum.

5. The process of claim 4, wherein the co-catalyst particles enhance combustion of carbon monoxide to carbon dioxide to a greater extent than the primary catalyst particles.

6. The process of claim 4, wherein the amount of the metal on the co-catalyst particles ranges from about 0.1 to about 10 weight percent, based on the total weight of the co-catalyst particles.

7. The process of claim 1, wherein the feedstock comprises an oxygenate and the product comprises light olefins.

8. The process of claim 7, wherein the co-catalyst particles have a second median particle diameter, which is less than the $d_{50}$.

9. The process of claim 7, wherein the co-catalyst particles have a median particle diameter of less than about 50 microns.

10. The process of claim 9, wherein the co-catalyst particles have a median particle diameter of less than about 40 microns.

11. The process of claim 7, wherein the plurality of catalyst particles has a first ARI, and the co-catalyst particles have a second API, and the ratio of the second ARI to the first ARI is from about 0.1 to about 1000.

12. The process of claim 11, wherein the ratio of the second ARI to the first ARI is greater than about 0.1 and less than 1.

13. The process of claim 11, wherein the ratio of the second ARI to the first API is from about 1 to about 1000.

14. The process of claim 13, wherein the ratio of the second ARI to the first ARI is from about 1 to about 100.

15. The process of claim 14, wherein the ratio of the second ARI to the first ARI is from about 1 to about 10.

16. The process of claim 7, wherein the plurality of catalyst particles has a first $k_{max}$ value and the co-catalyst particles have a second $k_{max}$ value, which is less than the first $k_{max}$ value.

17. The process of claim 16, wherein the second $k_{max}$ value is less than about 20 percent of the first $k_{max}$ value.

18. The process of claim 17, wherein the second $k_{max}$ value is less than about 10 percent otto first $k_{max}$ value.

19. The process of claim 18, wherein the second $k_{max}$ value is less than about 5 percent of the first $k_{max}$ value.

20. The process of claim 16, wherein the first $k_{max}$ value is greater than about 40 Hz.

21. The process of claim 20, wherein the first $k_{max}$ value is greater than about 80 Hz.

22. The process of claim 21, wherein the first $k_{max}$ value is greater than about 150 Hz.

23. The process of claim 16, wherein the second $k_{max}$ value is less than about 30 Hz.

24. The process of claim 23, wherein the second $k_{max}$ value is less than about 15 Hz.

25. The process of claim 24, wherein the second $k_{max}$ value is less than about 2 Hz.

26. The process of claim 7, wherein the co-catalyst particles comprise a molecular sieve selected from the group consisting of an ALPO, an all silica teolite, a dense phase crystalline aluminosilicate, SAPO-5, SAPO-8, SAPO-11, SAPO-16, SAPO-17, SAPO-18, SAPO-20, SAPO-31, SAPO-34, SAPO-35, SAPO-36, SAPO-37, SAPO-40, SAPO-41, SAPO-42, SAPO-44, SAPO-47, SAPO-56, AIE/CHA intergrowths, metal containing forms thereof, intergrown forms thereof, and mixtures thereof.

27. The process of claim 7, wherein the plurality of catalyst particles comprises a molecular sieve selected from the group consisting of SAPO-5, SAPO-8, SAPO-11, SAPO-16, SAPO-17, SAPO-18, SAPO-20, SAPO-31, SAPQ-34, SAPO-35, SAPO-36, SAPO-37, SAPO-40, SAPO-41, SAPO-42, SAPO-44, SAPO-47, SAPO-56, AEI/CHA intergrowths, metal containing forms thereof, intergrown forms thereof, and mixtures thereof.

28. The process of claim 7, wherein the plurality of catalyst particles has an ARI of from about 0.01 weight percent per hour to about 2.0 weight percent per hour.

29. The process of claim 28, wherein the plurality of catalyst particles has an ARI of from about 0.01 weight percent per hour to about 1.0 weight percent per hour.

30. The process of claim 7, wherein the plurality of catalyst particles has a first prime olefin selectivity ranging from about 75 weight percent to about 95 weight percent.

31. The process of claim 7, wherein the co-catalyst particles comprise a basic oxide or hydrotalcite, and optionally a rare earth metal component.

32. The process of claim 31, wherein addition of the co-catalyst particles in step (e) increases the lifetime of the plurality of catalyst particles.

33. The process of claim 31, wherein the co-catalyst particles are active for converting coke precursors to inactive compounds.

34. The process of claim 7, wherein the co-catalyst particles comprise a component selected from the group consisting of silica, alumina, alumninosilicates, clay and mixtures thereof.

35. A process for maintaining a particle size distribution in a reaction system, wherein the process comprises the steps of:
(a) providing a plurality of catalyst particles in a reaction zone, wherein the plurality of catalyst particles has a $d_2$ of at least about 7 microns, a first median particle diameter, and a $d_{90}$ of less than about 150 microns, and wherein the plurality of catalyst particles comprises primary catalyst particles;
(b) contacting the primary catalyst particles with a feedstock in the reaction zone under conditions effective to convert at least a portion of the feedstock to product;
(c) directing the product and at least a portion of the plurality of catalyst particles to a disengaging zone;
(d) increasing the first median particle diameter to a second median particle diameter by losing a portion of catalyst fines front the disengaging zone; and
(e) decreasing the second median particle diameter to a third median particle diameter by adding co-catalyst particles to the reaction system.

36. The process of claim 35, wherein the first median particle diameter is between about 75 and about 90 microbs, and the $d_{90}$ is no greater than about 120 microns.

37. The process of claim 35, wherein the feedstock comprises a regeneration medium and the product comprises combustion products, and wherein the co-catalyst particles enhance combustion of coke from the plurality of catalyst particles.

38. The process of claim 37, wherein the co-catalyst particles comprise a metal selected from the group consisting of: iron, cobalt, nickel, ruthenium, rhodium, palladium, osmium, iridium and platinum.

39. The process of claim 38, wherein the co-catalyst particles enhance combustion of carbon monoxide to carbon dioxide to a greater extent than the primary catalyst particles.

40. The process of claim 38, wherein the amount of the metal on the co-catalyst particles ranges from about 0.1 to about 10 weight percent, based on the total weight of the co-catalyst particles.

41. The process of claim 35, wherein the feedstock comprises an oxygenate and the product comprises light olefins.

42. The process of claim 41, wherein the co-catalyst particles have a fourth median particle diameter, which is less than the first median particle diameter.

43. The process of claim 41, wherein the co-catalyst particles have a fourth median particle diameter of less than about 50 microns.

44. The process of claim 43, wherein the fourth niedian particle diameter is less than about 40 microns.

45. The process of claim 41, wherein the plurality of catalyst particles has a first ARI, and the co-catalyst particles have a second API, and the ratio of the second AWl to the first ARI is from about 0.1 to about 1000.

46. The process of claim 45, wherein the ratio of the second ARI to the first ARI is greater than about 0.1 and less than 1.

47. The process of claim 45, wherein the ratio of the second ARI to the first ARI is from about 1 to about 1000.

48. The process of claim 47, wherein the ratio of the second API to the first ARI is from about to about 100.

49. The process of claim 46, wherein the ratio of the second ARI to the first ARI is from about 1 to about 10.

50. The process of claim 41, wherein the plurality of catalyst particles has a first $k_{max}$ value and the co-catalyst particles have a second $k_{max}$ value, which is less than the first $k_{max}$ value.

51. The process of claim 50, wherein the second $k_{max}$ value is less than about 20 percent of the first $k_{max}$ value.

52. The process of claim 51, wherein the second $k_{max}$ value is less than about 10 percent of the first $k_{max}$ value.

53. The process of claim 52, wherein the second $k_{max}$ value is less than about 5 percent of the first $k_{max}$ value.

54. The process of claim 50, wherein the first $k_{max}$ value is greater than about 40 Hz.

55. The process of claim 54, wherein the first $k_{max}$ value is greater than about 80 Hz.

56. The process of claim 55, wherein the first $k_{max}$ value is greater than about 150 Hz.

57. The process of claim 50, wherein the second $k_{max}$ value is less than about 30 Hz.

58. The process of claim 57, wherein the second $k_{max}$ value is less than about 15 Hz.

59. The process of claim 58, wherein the second $k_{max}$ value is less than about 2 Hz.

60. The process of claim 41, wherein the co-catalyst particles comprise a molecular sieve selected from the group consisting of an ALPO, an all silica zeolite, a dense phase crystalline aluminosilicate, SAPO-5, SAPO-8, SAPO-11, SAPO-16, SAPO-17, SAPO-18, SAPO-20, SAPO-31, SAPO-34, SAPO-35, SAPO-36, SAIPO-37, SAPO-40, SAPO-41, SAPO -42, SAPO-44, SAPO-47, SAPO-56, AEI/CHA intergrowths, metal containing forms thereof, intergrown forms thereof, and mixtures thereof.

61. The process of claim 41, wherein the plurality of catalyst particles comprises a molecular sieve selected from the group consisting of SAPO-5, SAPO-8, SAPO-11, SAPO-16, SAPO-17, SAPO-18, SAPO-20, SAPO-31, SALPO-34, SAPO-35, SAPO-36, SAPO-37, SAPO -40, SAPO-41. SAPO-42, SAPO-44, SAPO-47, SAPO-56, ABTICHA intergrowths, metal containing fbrms thereof, intergrown forms thereof, and mixtures thereof.

62. The process of claim 41, wherein the plurality of catalyst particles has an ARI of from about 0.01 weight percent per hour to about 2.0 weight percent per hour.

63. The process of claim 62, wherein the plurality of catalyst particles has an ARI of from about 0.01 weight percent per hour to about 1.0 weight percent per hour.

64. The process of claim 41, wherein the plurality of catalyst particles has a first prime olefin selectivity ranging from about 75 weight percent to about 95 weight percent.

65. The process of claim 41, wherein the co-catalyst particles comprise a basic oxide or hydrotalcite, and optionally a rare earth metal component.

66. The process of claim 65, wherein addition of the co-catalyst particles in step (e) increases the lifetime of the plurality oFeatalyst particles.

67. The process of claim 65, wherein the co-catalyst particles are active for converting coke precursors to inactive compounds.

68. The process of claim 41, wherein the co-catalyst particles comprise a component selected from the group consisting of silica, alumina, aluminosilicates, clay and mixtures thereof.

* * * * *